(12) United States Patent
Gupte et al.

(10) Patent No.: US 8,673,882 B2
(45) Date of Patent: Mar. 18, 2014

(54) INHIBITORS OF AUTOTAXIN

(75) Inventors: Renuka Gupte, Sylvania, OH (US);
Renukadevi Patil, Memphis, TN (US);
Gabor Tigyi, Memphis, TN (US);
Duane D. Miller, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/353,392

(22) Filed: Jan. 19, 2012

(65) Prior Publication Data

US 2012/0190650 A1    Jul. 26, 2012

Related U.S. Application Data

(60) Provisional application No. 61/461,555, filed on Jan. 20, 2011.

(51) Int. Cl.
*A61K 31/662* (2006.01)
*C07F 9/38* (2006.01)

(52) U.S. Cl.
USPC .................. 514/75; 514/134; 562/8; 562/9

(58) Field of Classification Search
USPC ..................... 562/8, 9; 514/75, 134
See application file for complete search history.

(56) References Cited

U.S. PATENT DOCUMENTS 3,929,450 A  *  12/1975  Hamm et al. ............... 504/127
2010/0016258 A1    1/2010  Lynch

OTHER PUBLICATIONS

Nishimasu, H, "Crytal structure of autotaxin and insight into GPCR activation by lipid mediators," Nature Structural & Molecular Biology, 18(2):205-213 (2011).
Vidot et al, Cell Signal, 22(6):926-935 (2010).
Durgam et al, Bioorg. Med. Chem. Lett., 16(3):633-640 (2006).
Albers et al, J. Med. Chem., 53(13):4958-4967 (2010).
Albers et al, Proc. Natl. Acad. Sci., 107(16):7257-7262 (2010).
Baker et al, J. Biol. Chem., 281(32):22786-22793 (2006).
Gajewiak et al, Org. Lett., 10(6):1111-1114 (2008).
Gajewiak et al, ChemMedChem., 2(12):1789-1798 (2007).
Zhang et al, Cancer Res., 69(13):5441-5449 (2009).
Uchiyama et al, Biochim. Biophys. Acta, 1771(1):103-112 (2007).
Ferry et al, J. Pharmacol. Exp. Ther., 327(3):809-819 (2008).
International Search Report from PCT/US12/21818 Mailed on May 8, 2012.

* cited by examiner

*Primary Examiner* — Yong Chu
*Assistant Examiner* — Karen Cheng
(74) *Attorney, Agent, or Firm* — Lathrop & Gage LLP; Brian C. Trinque

(57) ABSTRACT

Stabilized benzyl phosphonic acid and naphthyl phosphonic acid analog compounds are effective in inhibiting the activity of autotaxin.

3 Claims, 10 Drawing Sheets

INHIBITORS OF AUTOTAXIN

This application claims priority from pending U.S. Provisional Patent Application Ser. No. 61/461,555 which was filed on Jan. 20, 2011, which application is incorporated herein by reference in its entirety.

Pursuant to 35 U.S.C. §202, it is hereby acknowledged that the U.S. Government has certain rights in the invention described herein, which was supported in part by United States National Cancer Institute—National Institutes of Health grant #CA92160

BACKGROUND OF THE INVENTION

Autotaxin (ATX) is a member of the nucleotide pyrophosphate (NPP) family of enzymes. ATX is also known as ectonucleotide pyrophosphatase/phosphodiesterase 2 (NPP2). ATX catalyzes the hydrolysis of lysophosphatidylcholine (LPC) to lysophosphatidic acid (LPA).

ATX is required for normal development. As reported in Tanaka et al, J. Biol. Chem., 281 (35):25822-25830 (2006); and van Meeteren et al, Mol. Cell Biol., 26 (13):5015-5022 (2006), homozygous ATX knockout mice die in utero at day 9.5, coinciding with a period of vascular stabilization. As reported in Fotopoulou et al, Dev. Biol. 2010, 339 (2):451-464 (2010), ATX also is important in development of the nervous system as ATX knockout mice show defects in neural tube development.

LPA is a signaling molecule that acts as a potent mitogen by activating G-protein coupled receptors. LPA is also a mitogen and an anti-apoptotic agent, which provides survival advantages to carcinomas that utilize LPA. Certain cancers, such as ovarian cancers, produce high levels of LPA.

ATX is one of the most upregulated genes in highly metastatic cancers, as reported in Luer et al, Anticancer Res., 22 (2A):733-740 (2002). Liu et al, Cancer Cell, 15 (6):539-550 (2009) reported that ectopic expression of ATX in mice leads to mammary intraepithelial neoplasia, which develops into invasive and metastatic tumors. Samadi et al, Oncogene. 28 (7):1028-1039 (2009) reported that ATX inhibits paclitaxel-induced apoptosis in breast cancer cells, and E et al, J. Biol. Chem., 284 (21):14558-14571 (2009) reported that LPA renders ovarian cancer cells chemoresistant to cisplatin and adriamycin. Jazaeti et al, Clin. Cancer Res., 11 (17):6300-6310 (2005) reported that ATX is also overexpressed in patients with recurrent disease after prior treatment with chemotherapy. In a genome-wide siRNA screen, Vidot et al, Cell Signal., 22 (6):926-935 (2010) identified ATX as a candidate drug-resistance gene in ovarian cancer.

The ATX-LPC-LPA receptor axis is a promising therapeutic target for the management of cancer metastasis and therapeutic resistance. As reported in Tsuda et al, J. Biol. Chem., 281 (36):26081-26088 (2006); and van Meeteren et al, J. Biol. Chem., 280 (22):21155-21161 (2005), ATX shows feedback inhibition by its hydrolysis products LPA, CPA, and sphingosine-1-phosphate (S1P). Thus, many initially identified ATX inhibitors are lipid-like substrate or product analogs, as reported in Durgarn et al, Bioorg. Med. Chem. Lett., 16 (3):633-640 (2006); Albers et al, J. Med. Chem., 53 (13):4958-4967 (2010); Albers et al. Proc. Natl. Acad. Sci., 107 (16):7257-7262 (2010); Baker et al, J. Biol. Chem., 281 (32):22786-22793 (2006); Gajewiak et al, Org. Lett., 10 (6):1111-1114 (2008); Gajewiak et al, Chem. Med. Chem., 2 (12): 1789-1798 (2007); Zhang, et al, Cancer Res., 69 (13):5441-5449 (2009); and Uchiyama et al, Biochim. Biophys, Acta, 1771 (1):103-112 (2007). However, the characteristics of such lipid-like compounds limit their utility as potential lead compounds for drug development.

Recently, Ferry et al, J. Pharmacol. Exp. Ther., 327 (3): 809-819 (2008), described a non-lipid ATX inhibitor 4-tetradecanoylaminobenzyl phosphonic acid (S32826) that possessed nanomolar activity in-vitro. Unfortunately, S32826 failed to show activity in cellular and in-vivo systems. Hydrolysis of the amide bond present in S32826 could be the reason for its instability and thus lack of activity in cellular systems. The structure of S32826 is shown below as Formula A.

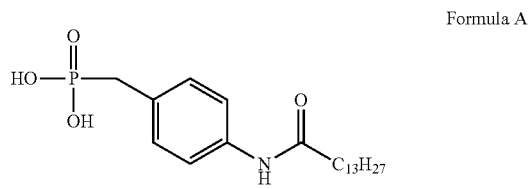

Formula A

Thus, a significant need exists for a chemical compound that is an inhibitor of ATX and that is active in cellular systems.

BRIEF DESCRIPTION OF THE DRAWINGS

In FIG. 1, $R_4$=alkyl $C_{11}H_{23}$ to $C_{23}H_{47}$ or alkenyl $C_{11}H_{21}$ to $C_{23}H_{45}$, (a)=PD(OAc)$_2$, Et$_3$N, DMF, Reflux; (b)=H$_2$/Pd/C, MeOH; (c)=LAH, THF, at 0° C. to RT; (d)=PBr$_3$, Ether, at RT; (e)=P(OMe)$_3$, Reflux; (f)=TMSBr, CH$_3$CN, Reflux; (g) MeOH, RT; (h) Lawesons Reagent, Tolune, Reflux; (i)=bis(2-cyanoethyl)-N,N-diisopropylphosphoramadite, 1H-tetrazole, H$_2$O$_2$, DCM; (j)=bis(2-cyanoethyl)-N,N-diisopropylphosphoramadite, 1H-tetrazole, DCM, RT & Sulfur, Reflux; (k)=KOH, MeOH & dil HCl.

In FIG. 2, $R_4$=alkyl $C_{11}H_{23}$ to $C_{23}H_{47}$ or alkenyl $C_{11}H_{21}$ to $C_{23}H_{45}$, (a)=PD(OAc)$_2$, Et$_3$N, DMF, Reflux; (b)=H$_2$/Pd/C, MeOH; (c)=LAH, THF, at 0° C. to RT; (d)=PBr$_3$, Ether, RT; (e)=P(OMe)$_3$, Reflux; (f)=TMSBr, CH$_3$CN, Reflux; (g) MeOH, RT; (h) Lawesons Reagent, Tolune, Reflux; (i)=bis(2-cyanoethyl)-N,N-diisopropylphosphoramadite, 1H-tetrazole, H$_2$O$_2$, DCM; (j)=bis(2-cyanoethyl)-N,N-diisopropylphosphoramadite, 1H-tetrazole, DCM, RT & Sulfur, Reflux; (k)=KOH, MeOH & dil HCl.

In FIG. 3, $R_5$=alkyl $C_6H_{13}$ to $C_{23}H_{47}$ or alkenyl $C_6H_{11}$ to $C_{23}H_{45}$, (a)=PD(OAc)$_2$, Et$_3$N, DMF, Reflux; (b)=H$_2$/Pd/C, MeOH; (c)=LAH, THF, at 0° C. to RT; (d)=PBr$_3$, Ether, RT; (e)=P(OMe)$_3$, Reflux; (f)=TMSBr, CH$_3$CN, Reflux; (g) MeOH, RT; (h) Lawesons Reagent, Tolune, Reflux; (i)=bis(2-cyanoethyl)-N,N-diisopropylphosphoramadite, 1H-tetrazole, H$_2$O$_2$, DCM; (j)=bis(2-cyanoethyl)-N,N-diisopropylphosphoramadite, 1H-tetrazole, DCM, RT & Sulfur, Reflux; (k)=KOH, MeOH & dil HCl.

In FIG. 4, compound 1=4-aminobenzylphosphonic acid diethyl ester; compound 2=1-hexadecanesulfonyl chloride; compound 3=4-(hexadecylsulfonamido)benzylphosphonate;

(a)=N,N-diisopropylethylamine, TMF, reflux, 24 h; (b)=TMSBr, CH₃CN, reflux, 1 h; and (c)=MeOH, 30 min, RT.

Figure 5:
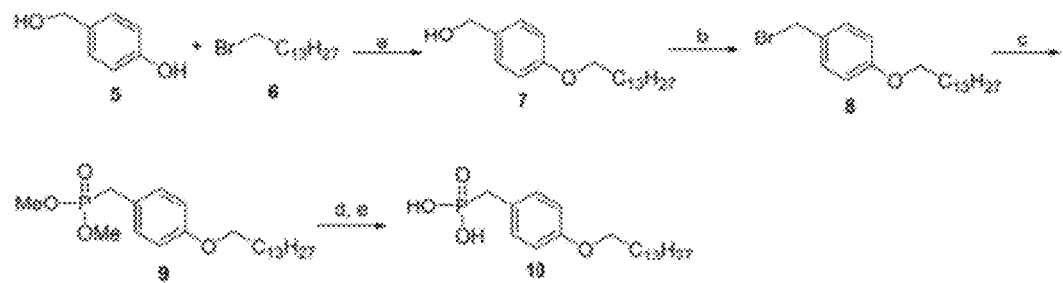

FIG. 5 shows a synthetic scheme for the synthesis of Compound 10. In FIG. 5, compound 5=4-hydroxymethylphenol; compound 6=1-bromotetradecane; (a)=K₂CO₃, 18-crown-6, acetone, reflux, 16 h; (b)=PBr₃, ether, RT, 30 min; (c)=P(OMe)₃, reflux 18 h; (d)=TMSBr, CH₃CN, reflux, 1 h; and (e)=MeOH, 30 min, RT.

Figure 6:
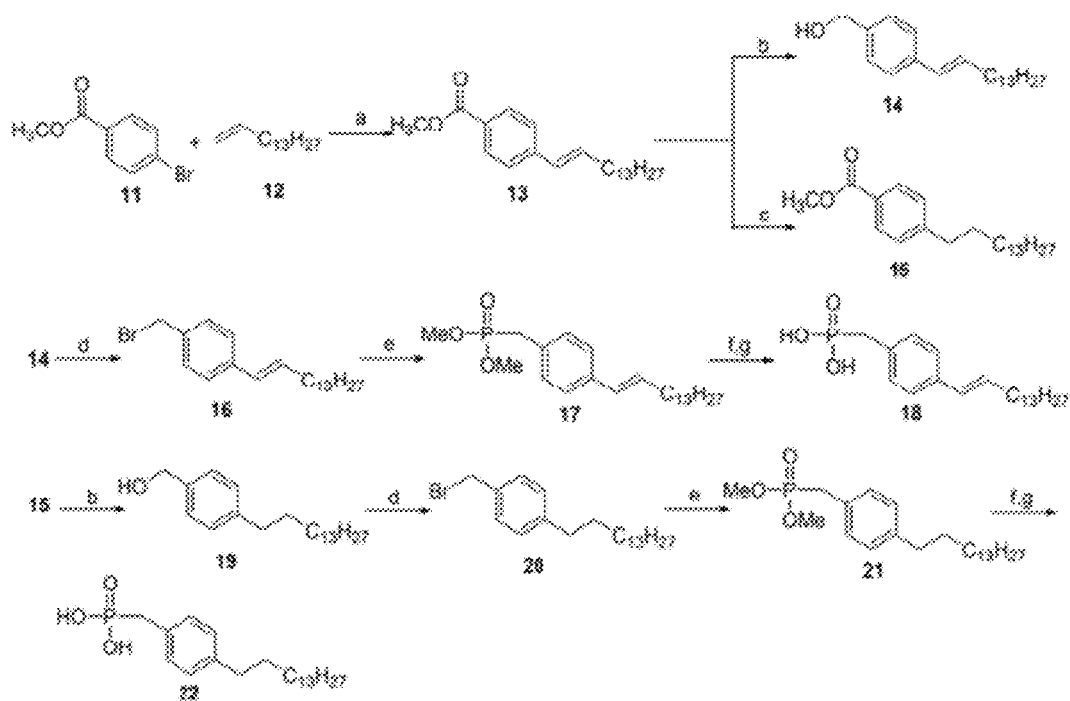

FIG. 6 shows a synthetic scheme for the synthesis of Compound 18 ((E)-4-(pentadec-1-enyl)benzylphosphonic acid) and Compound 22 (4-pentadecylbenzylphosphonic acid). In FIG. 6, (a)=Pd(OAc)₂, Et₃N, DMF, reflux, 16 h; (b)=LAH, THF, 0° C. to RT, 4 h; (c)=H₂/Pd/C, MeOH; (d)=PBr₃, ether, RT, 30 min; (e)=P(OMe)₃, reflux, 18 h; (f)=TMSBr, CH₃CN, reflux, 1 h; and (g)=MeOH, 30 min, RT.

Figure 7:
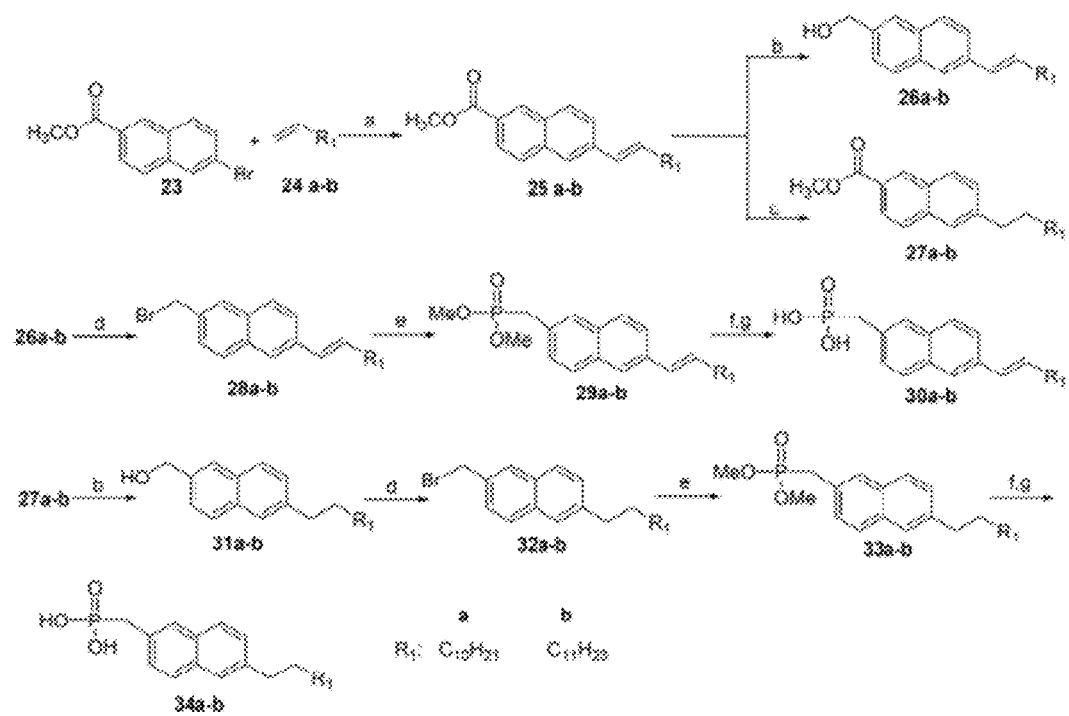

FIG. 7 shows a synthetic scheme for the synthesis of 6-substituted naphthalen-2-yl-methyl phosphonic acid analogs compounds 30a, 30b, 34a, and 34b. In FIG. 7, (a)=Pd(OAc)₂, Et₃N, DMF, reflux, 16 h; (b)=LAH, THF, 0° C. to RT, 4 h; (c)=H₂/Pd/C, MeOH; (d)=PBr₃, ether, RT, 30 min; (e)=P(OMe)₃, reflux, 18 h; (f)=TMSBr, CH₃CN, reflux, 1 h; and (g)=MeOH, 30 min, RT.

Figure 8:
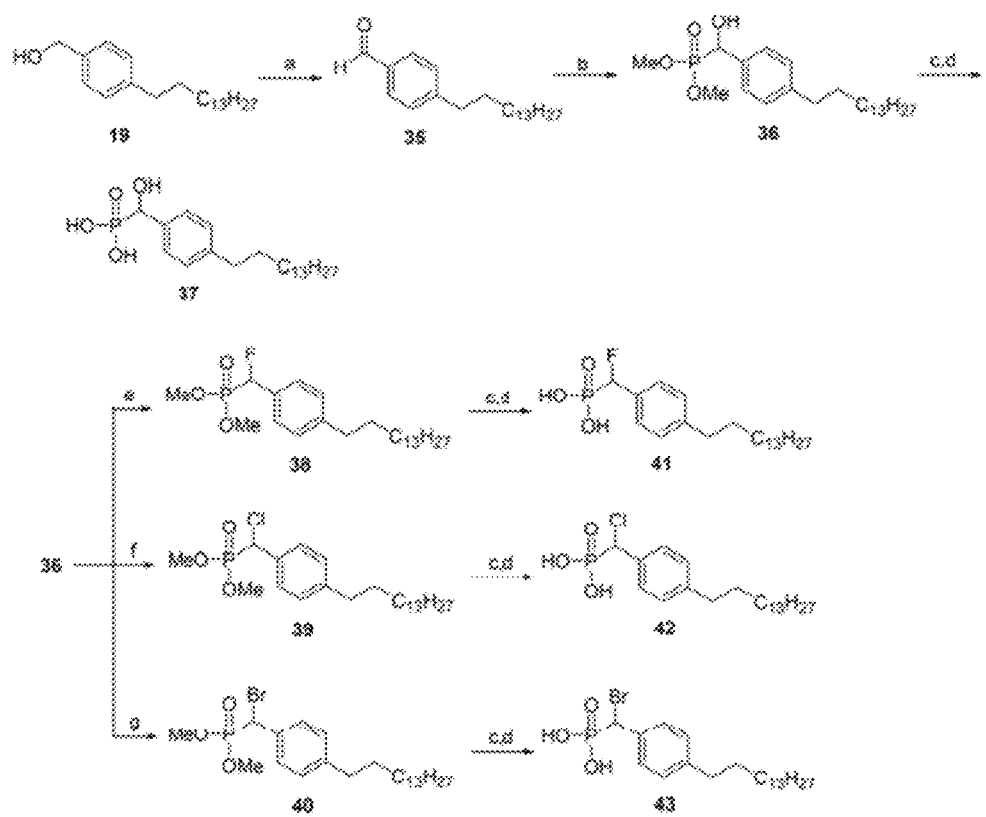

FIG. 8 shows a synthetic scheme for the synthesis of compounds 37, 41, 42, and 43. In FIG. 8, (a)=PDC, CH₂Cl₂, RT, 16 h; (b)=HP(O)(OCH₃)₂, Et₃N, 0° C. to RT, 4 h; (c)=TMSBr, CH₃CN, reflux, 1 h; (d)=MeOH, 30 min, RT; (e)=DAST, ether, 0° C. to RT, 1 h; (f)=SOCl₂, CH₂Cl₂, reflux, 1 h; and (g)=PBr₃, ether, RT, 30 min.

Figure 9:
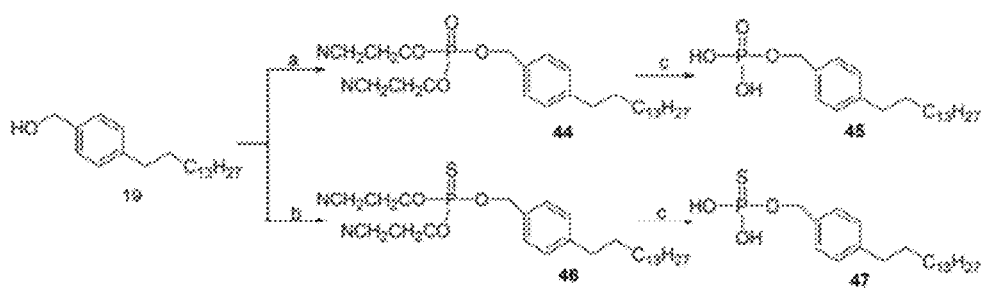

FIG. 9 shows a synthetic scheme for the synthesis of compounds 45 and 47. In FIG. 9, (a)=bis(2-cyanoethyl)-N,N-diisopropylphosphoramidite, 1H-tetrazole, CH₂Cl₂, RT, followed by 50% H2O2; (b)=bis(2-cyanoethyl)-N,N-diisopropylphosphoramidite, 1H-tetrazole, CH₂Cl₂, RT, followed by sulfur, reflux, 2 h; (c)=KOH, MeOH, followed by dil HCl.

Figure 10:
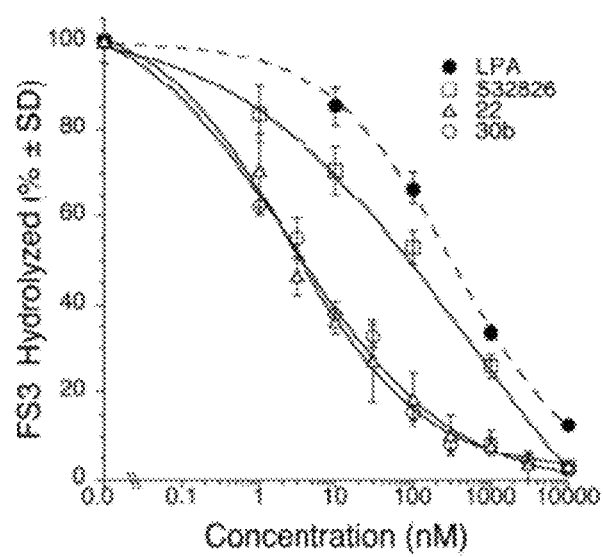

FIG. 10 is a graph showing the inhibition of ATX-mediated hydrolysis of FS3 by LPA (●), S32826 (□), compound 22 of the present application (Δ), and compound 30 b of the present application (○).

Figure 11:
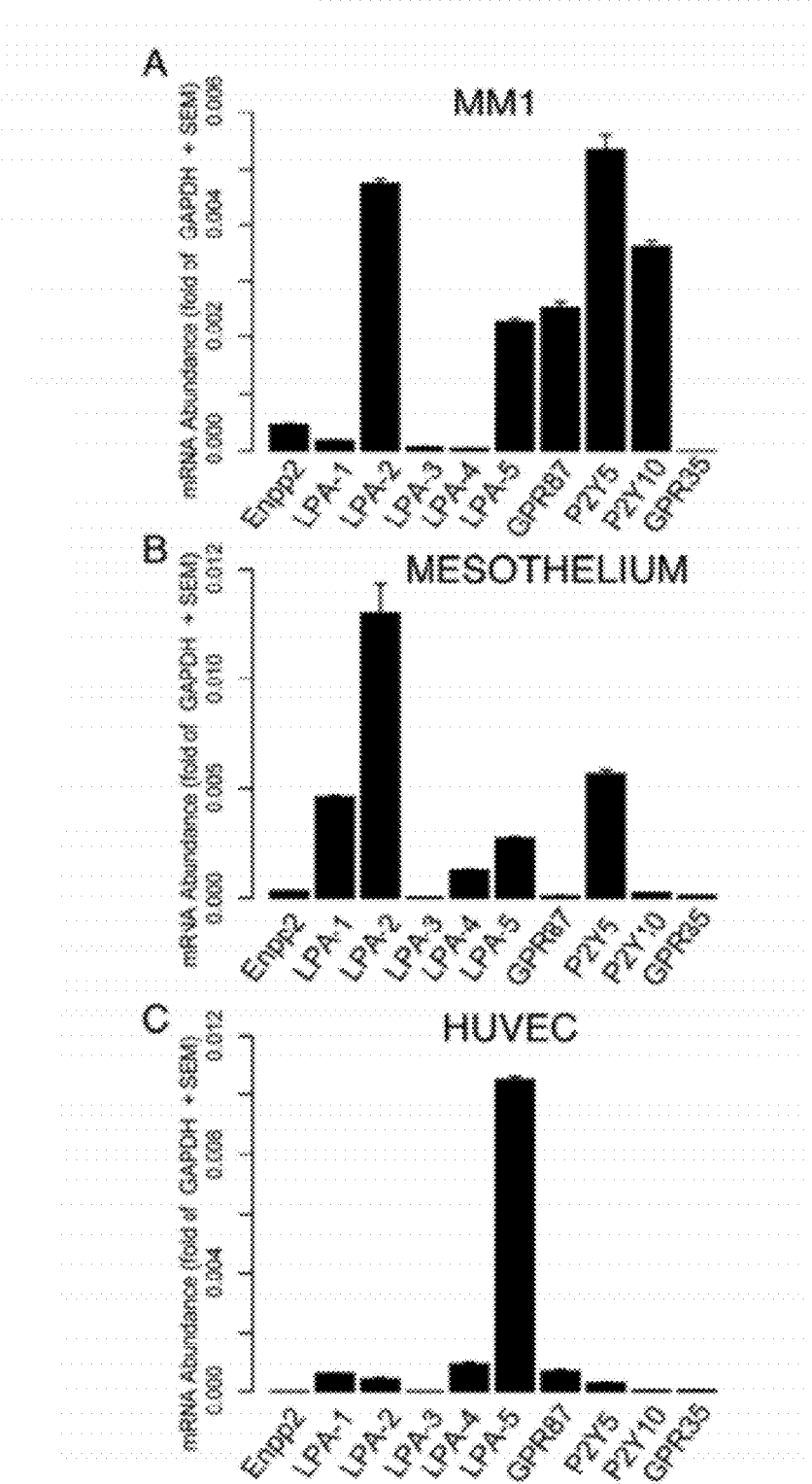

FIG. 11 is a set of graphs showing the profile of LPA receptor and ATX transcripts in MM1 rat hepatocarcinoma cells (panel A), mesothelial cells from C57BL/6 mice (panel b), and HUVEC cells.

Figure 12:
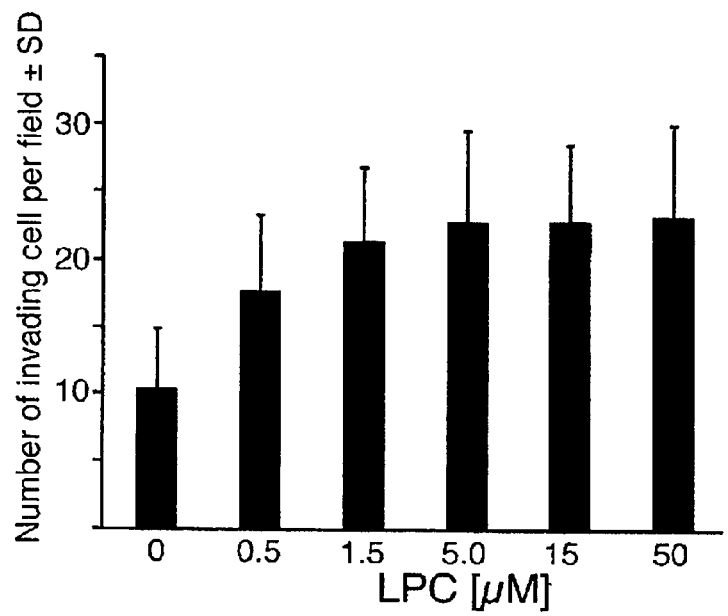
Figure 12:
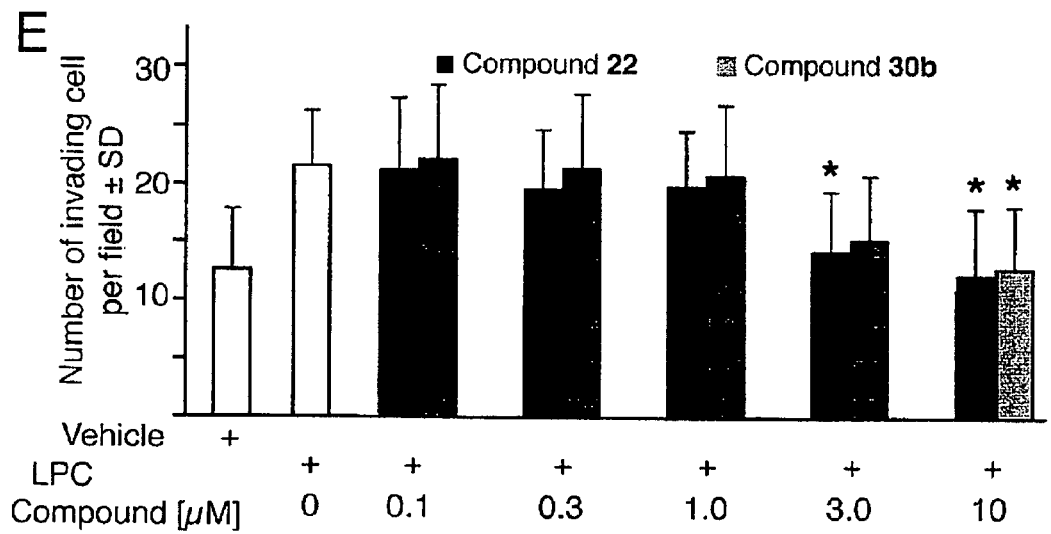

FIG. 12 is a set of graphs showing the LPC dose-dependent invasion of mesothelial cell layers by MM1 cells (panel D) and the inhibition of invasion of the mesothelial cell layers by compounds 22 and 33b of the present application (panel E).

Figure 13:
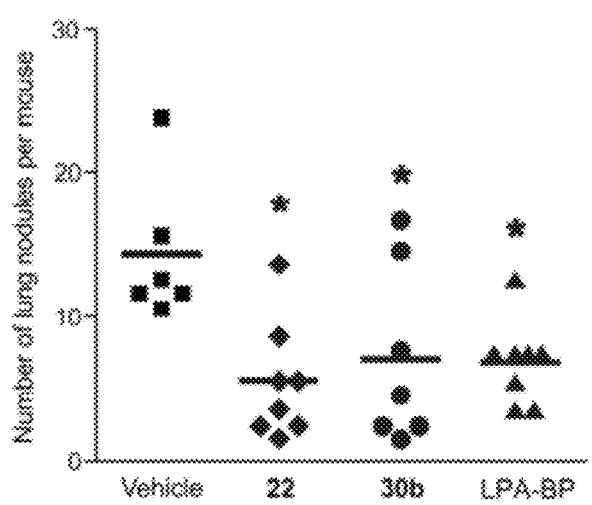

FIG. 13 is a graph showing the effect of compounds of the present application in reducing lung metastasis from a melanoma. In FIG. 13, *denotes p<0.05 relative to vehicle.

Figure 14:
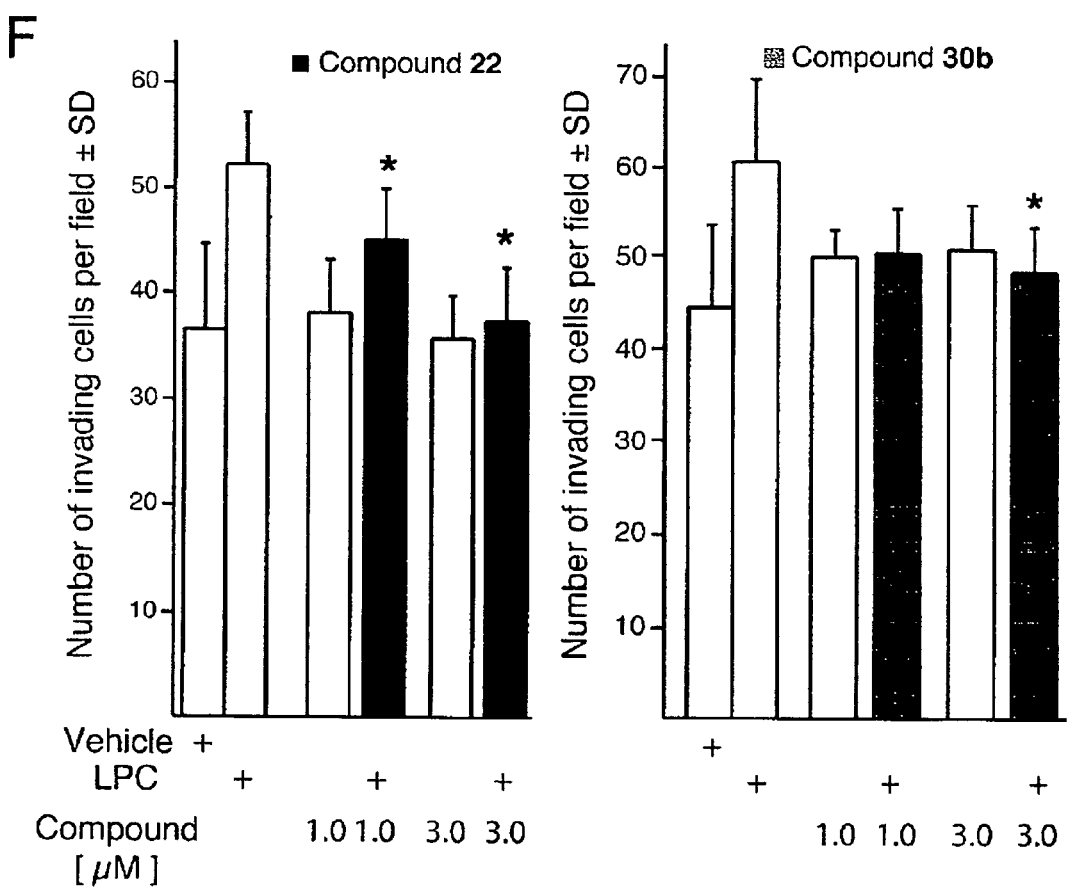

FIG. 14 is a pair of graphs showing the blockage by compounds 22 and 33b of the present application of LPC-induced invasion of HUVEC cells by MM1 cells (panel F).

The following abbreviations are used in the figures and in the following description of the invention:
Pd(OAC)₂=Palladium (II) acetate; Et₃N=Triethyl amine; DMF=Dimethyl formamide; LAH=Lithium aluminum hydride; THF=Tetrahydrofuran; PBr₃=Phosphorous tribromide; P(OMe)₃=Trimethyl phosphate; PDC=Pyridinium dichromate; TMSBr=Timethylsilyl bromide; DAST=Diethylaminosulfur trifluoride; CH₃CN=Acetonitrile; MeOH=Methanol; H₂O₂=Hydrogen peroxide; DCM=Dichloromethane; EtOAc=Ethyl acetate; DMSO=Dimethyl sulfoxide; KOH=Potassium hydroxide; K₂CO₃=Potassium carbonate; MgSO₄=Magnesium sulfate; HCl=Hydrochloric acid; SOCl₂=Thionyl chloride; RT=Room temperature; Equiv=Equivalent; ATX=Autotaxin; LPC=Lysophosphatidylcholine; LPLD=Lysophospholipase D; LPA=Lysophosphatidic acid; CPA=Cyclophosphatidic acid; S1P=Sphingosine-1-phosphate; LPAR=Lysophosphatidic acid receptors; LPA-BP=LPA bromophosphonate; HUVEC=Human umbilical cord vascular endothelial cell; NMR=Nuclear Magnetic resonance; ESI=Electrospray/ion; HRMS=High-resolution mass; TLC=Thin-layer chromatography

DETAILED DESCRIPTION OF THE INVENTION

It is conceived by the current inventors that the reason for the lack of activity of S32826 in cellular systems is due to instability of this compound and it is further conceived that this lack of activity is due to hydrolysis of the amide bond present in S32826. In accordance with this conception, analogs of S32826 were developed that lack the amide bond of S32826. Such stabilized analogs have been determined to inhibit ATX with potencies that are comparable to that of S32826. The stabilized analogs inhibit ATX in a mixed-mode mechanism and have been shown to not significantly inhibit the related lysophospholipid phosphodiesterases NPP6 and NPP7 or to have an effect on LPA receptors. The stabilized ATX analogs were shown to inhibit ATX-dependent invasion of cancer cells into cell culture monolayers in vitro. In addition, the ATX analogs showed a profound reduction in lung foci in vivo using a murine model of melanoma metastasis.

In a preferred embodiment, the stabilized ATX inhibitor chemical compound of this application has the formula shown below as Formula B.

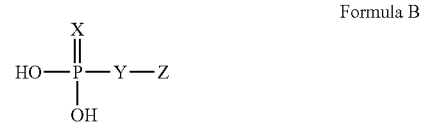

Formula B wherein;
X is O or S,
Y is selected from —(CH₂)n-, —CH(OH)—, —CH(F)—, —CH(Br)—, —CH(Cl)—, —O(CH₂)n-, and
n is an integer from 1-3, and
Z is an aryl or heteroaryl ring system, wherein
when Z is phenyl or heteroaryl, one or more of the positions of the ring system may be optionally substituted with H, C₁₃₋₂₅ alkyl, C₁₃-C₂₅ alkenyl, F, Cl, Br, I, CH₃, OCH₃, CF₃, OCF₃, NO₂, NH₂, NR₂, or NHSO₂R₃ wherein R₂ and R₃ is alkyl, and when Z is naphthalenyl, one or more of positions of the ring system may be optionally substituted with H, C₈₋₂₅ alkyl, C₈-C₂₅ alkenyl, F, Cl, Br, I, CH₃, OCH₃, CF₃, OCF₃, NO₂, NH₂, NR₂, or NHSO₂R₃ wherein R₂ and R₃ is alkyl.

In a preferred embodiment, the ATX inhibitor chemical compound is a benzyl phosphonic acid derivative as shown in Formula C:

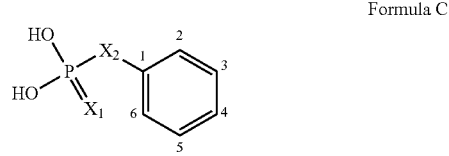

Formula C wherein $X_1$ is O or S, $X_2$ is $CH_2$, $CH_2CH_2$, $CH_2CH_2CH_2$, CHOH, CHF, CHBr, CHCl, $OCH_2$ or $OCH_2CH_2$, a) the 6-membered ring may contain from one to three nitrogen atoms at the C positions 2, 3, 4, 5, and 6. For the case wherein the 6-membered ring has three nitrogens, at most two of the nitrogens are adjacent to one another b) one or more of positions 2, 3, 4, 5, and 6 are H, F, Cl, Br, I, $CH_3$, $OCH_3$, $CF_3$, $OCF_3$, $NO_2$, $NH_2$, $NR_2$, or $NHSO_2R_3$, wherein $R_2$ and $R_3$ are alkyl, and c) any one of positions 2 to 6 is alkyl, preferably $C_{13}$-$C_{25}$ alkyl, or alkenyl, preferably $C_{13}$-$C_{25}$ alkenyl.

In another preferred embodiment, the ATX inhibitor chemical compound is a naphthyl phosphonic acid derivative as shown in Formula D:

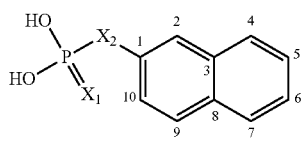

Formula D wherein $X_1$ is O or S, $X_2$ is $CH_2$, $CH_2CH_2$, $CH_2CH_2CH_2$, CHOH, CHF, CHBr, CHCl, $OCH_2$ or $OCH_2CH_2$, a) one or more of positions 2, 4, 5, 6, 7, 9 and 10 are H, F, Cl, Br, I, $CH_3$, $OCH_3$, $CF_3$, $OCF_3$, $NO_2$, $NH_2$, $NR_2$, or $NHSO_2R_3$, wherein $R_2$ and $R_3$ are alkyl, and c) any one of positions 2, 4, 5, 6, 7, 9, and 10 is alkyl, preferably $C_8$-$C_{25}$ alkyl, or alkenyl, preferably $C_8$-$C_{25}$ alkenyl.

As used herein, the term "aryl" means an unsaturated, aromatic monocyclic ring of 6 carbon members or to an unsaturated, aromatic polycyclic ring of from 10 to 14 carbon members. Examples of aryl rings include, and are not limited to, phenyl, naphthalenyl, and anthracenyl.

As used herein, the term "heteroaryl" means an aromatic ring of 5 or 6 carbon members wherein the ring contains one or more carbon atoms and at least one atom other than carbon. Such suitable heteroatoms include nitrogen, oxygen, and sulfur in the case of 5-membered rings, the heteroaryl ring contains one member of nitrogen, oxygen or sulfur and, in addition may contain up to three additional nitrogens. In the case of 6 membered rings, the heteroaryl ring may contain from one to three nitrogen atoms. For the case wherein the 6-membered ring has three nitrogens, at most two of the nitrogens are adjacent to one another. The term "heteroaryl" includes a heteroaryl ring fused to a benzene ring.

Examples of heteroaryl groups include, but are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pryidinyl, pyridazinyl, pryimidinyl and pyrazinyl. Examples of fused heteroaryl groups include indolyl, isoindolyl, indolinyl, benzofuryl, benzothienyl, indazolyl, benzimidazolyl, quinolizinyl, quinolinyl, isoquinolinyl, and quinazolinyl.

Examples of aryl and heteroaryl groups in which one or more carbons of the aryl ring system are substituted with nitrogen are shown below in Formula E.

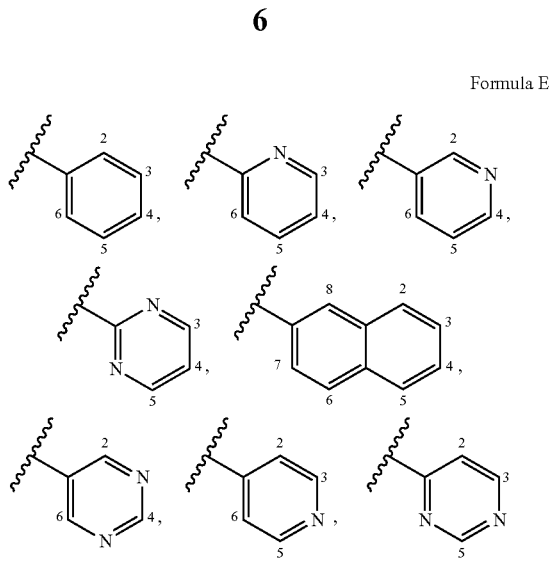

Formula E

As used herein, the term "alkyl," whether used alone or, as part of a substituent group, refers to straight and branched carbon chains having 8 to 25 carbon atoms or any number within this range and the term "alkenyl," whether used alone or as part of a substituent group, refers to straight and branched carbon chains having 8 to 25 carbon atoms or any number within this range, wherein an alkenyl chain has at least one double bond in the chain.

The novel compounds encompassed by the instant application are those described above, and the salts, such as but not limited to ammonia, potassium, sodium, and enantiomers, diastereomers, pro-drugs, and/or pharmaceutical compositions thereof.

Figure 1:
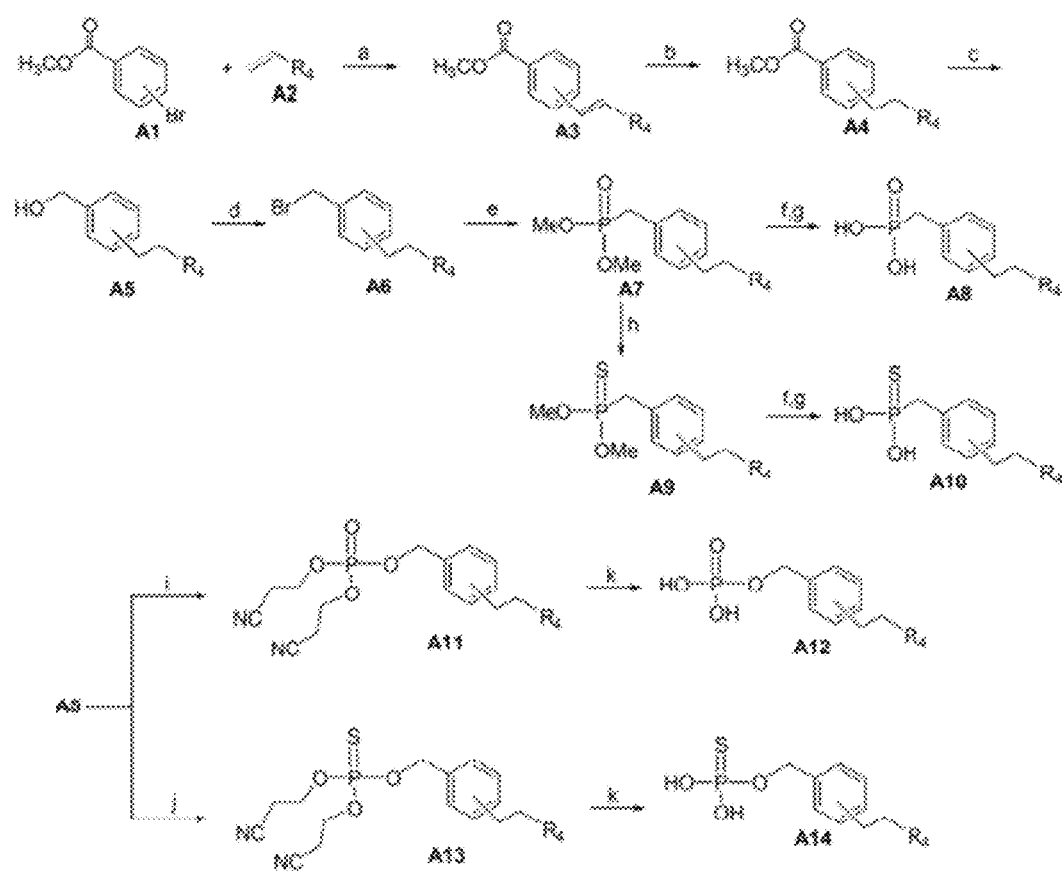
FIG. 1 shows a general scheme for synthesis of the benzyl phosphonic acid analogs of the present application as shown in Formula C.
Figure 2:
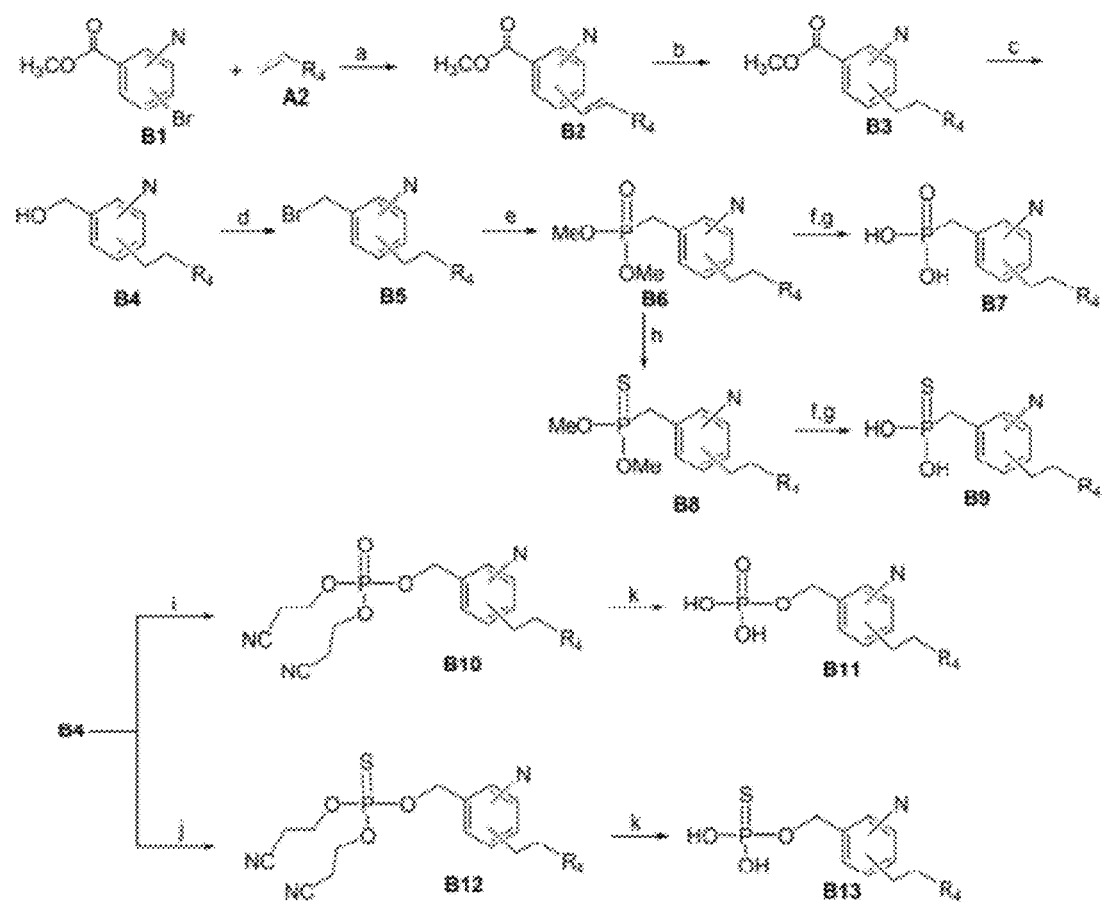
FIG. 2 shows a general scheme for synthesis of the N-substituted benzyl phosphonic acid analogs of the present application as shown in Formula C.
Figure 3:
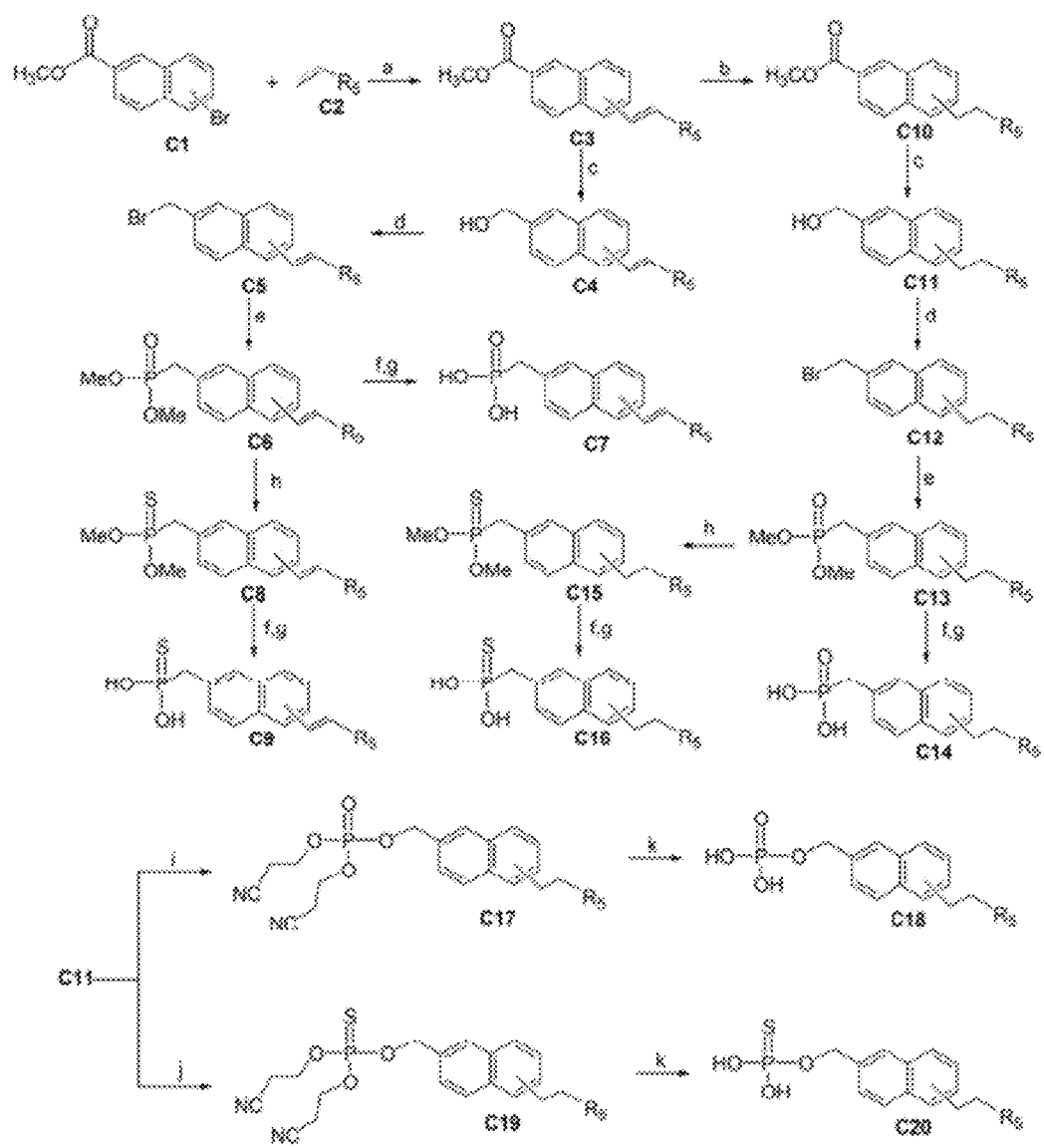
FIG. 3 shows a general scheme for synthesis of the naphthyl phosphonic acid analog, of the present application as shown in Formula D.
Figure 4:
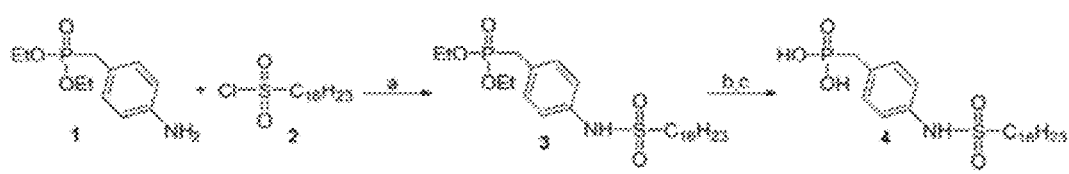
FIG. 4 shows a synthetic scheme for the synthesis of Compound 4 (4-hexadecane-1-sulfonylamino)benzyl phosphonic acid.

FIGS. 1 to 3 show general schemes for synthesis of the stabilized ATX inhibitor chemical compounds of the present application, as shown in Formulas B to D. The starting materials and the reagents used in the schemes are commercially available or are readily prepared by methods known to those skilled in the art. It is to be noted that the general schemes are an illustration and are not to be construed as limitations on the chemical reactions and the conditions expressed.

FIG. 1 shows a general scheme for synthesis of the benzyl phosphonic acid analog ATX inhibitor chemical compounds of the present application as shown in Formula C. As shown in FIG. 1, the Heck coupling of compound A1 with an appropriate alkene (A2) using a palladium catalyst such as Palladium (II) acetate, and a tertiary amine such as triethyl amine in DMF provides the unsaturated compound A3 which upon catalytic hydrogenation using a palladium catalyst such as Pd/C in a polar solvent such as MeOH provides compound A4. Compound A4 is reduced to the corresponding alcohol using a reducing agent such as LAH in THF to produce compound A5. Conversion of the alcohol A5 to a bromide derivative (A6) is achieved by reaction with a brominating agent such as $PBr_3$ in ether, which is then subjected to the Michealis-Arubuzov reaction in the presence of trimethylphosphite to yield the compound A7. Removal of the methyl groups is accomplished by treating A7 with TMSBr in acetonitrile followed by the addition of MeOH to give the desired phosphonic acid derivative A8.

Alternatively, the treatment of compound A7 with Lawesons reagent in a solvent such as toluene provides the compound A9, which is then reacted with TMSBr followed by MeOH to yield the thiophosphonic acid derivative A10. Alternatively, reaction of the alcohol derivative A5 with 1H-tetrazole, bis(2-cyanoethyl) N,N-diisopropylphosphoramidite. $H_2O_2$ and 1H-tetrazole, bis(2-cyanoethyl) N,N-diisopropylphosphoramidite, elemental sulfur in DCM provides bis-cyanoethyl protected phosphoric acid methyl ester derivative A11 and bis-cyanoethyl protected thiophosphoric acid methyl ester derivative A13, respectively. Removal of the bis-cyano ethyl groups is obtained by reaction with a base such as KOH in MeOH followed by acidification using an aqueous acid such as HCl provides phosphoric acid methyl ester derivative A12 and thiophosphoric acid methyl ester derivative A14.

FIG. 2 shows a general scheme for synthesis of the N-substituted benzyl phosphonic acid analog ATX inhibitor chemical compounds of the present application as shown in Formula C. As shown in FIG. 2, the Heck coupling, of compound B1 with an appropriate alkene (A2) using a palladium catalyst such as palladium (II) acetate, and a tertiary amine such as triethyl amine in DMF provides the unsaturated compound B2, which upon catalytic hydrogenation using a palladium catalyst such as Pd/C in a polar solvent such as MeOH provides compound B3. Compound B3 is reduced to the corresponding alcohol using a reducing agent such as LAH in THF to produce compound B4. Conversion of the alcohol B4 to a bromide derivative B5 is achieved by reaction with a brominating agent such as $PBr_3$ in ether, which is then subjected to the Michealis-Arubuzov reaction in the presence of trimethylphosphite to yield the compound B6. Removal of the methyl groups is accomplished by treating B6 with TMSBr in acetonitrile followed by the addition of MeOH to give the desired phosphonic acid derivative B7.

Alternatively, the treatment of compound B6 with Lawesons reagent in a solvent such as toluene provides the compound B8, which is then reacted with TMSBr followed by MeOH to yield the thiophosphonic acid derivative B9. Alternatively, reaction of the alcohol derivative B4 with 1H-tetrazole, bis(2-cyanoethyl) N,N-diisopropylphosphoramidite, $H_2O_2$ and 1H-tetrazole, bis(2-cyanoethyl) N,N-diisopropylphosphoramidite, elemental sulfur in DCM provides bis-cyanoethyl protected phosphoric acid methyl ester derivative B10 and bis-cyanoethyl protected thiophosphoric acid methyl ester derivative B12, respectively. Removal of the bis-cyano ethyl groups is obtained by reaction with a base such as KOH in MeOH followed by acidification using an aqueous acid such as HCl provides phosphoric acid methyl ester derivative B11 and thiophosphoric acid methyl ester derivative B13.

FIG. 3 shows a general scheme for synthesis of the naphthyl phosphonic acid analog ATX inhibitor chemical compounds of the present application as shown in Formula D. As shown in FIG. 3, substituted naphthyl bromide (C1) reacts with an alkene (C2) under the Heck reaction conditions to afford the compound C3. Reduction of the ester derivative (C3) to the alcohol using a reducing agent such as LAH in an ethereal solvent such as THF yields the compound C4, which is treated with a brominating reagent such as $PBr_3$ in ether to produce the bromide derivative (C5). The Michealis-Arubuzov reaction of compound C5 using trimethylphosphite gives the phosphonic acid dimethyl ester derivative (C6), which is then treated with the Lawesons reagent in toluene to furnish thiophosphonic acid dimethyl ester derivative (C8). Treatment of the compounds C6 and C8 with TMSBr in acetonitrile followed by the addition of MeOH yields the desired phosphonic acid derivative (C7) and thiophosphonic acid derivative (C9), respectively. Catalytic hydrogenation of compound C3 using a palladium catalyst such as, Pd/C in in an alcohol such as MeOH produces the saturated compound C10, which in turn, is subjected to reduction by using a reducing agent such as LAH in THF to provide the alcohol derivative (C11). Conversion of the compound C11 to a bromide derivative (C12) is accomplished by reaction with a brominating agent such as $PBr_3$ in ether, which is then subjected to the Michealis-Arubuzov reaction using trimethylphosphite to afford the compound C13. Reaction of compound C13 with the Lawesons reagent yields the compound C15. Treatment of compounds C13 and C15 with TMSBr followed by MeOH gives phosphonic acid derivative (C14) and thiophosphonic acid derivative (C16), respectively. Alternatively, treatment of the compound C11 with 1H-tetrazole, bis(2-cyanoethyl) N,N-diisopropylphosphoramidite, $H_2O_2$ and 1H-tetrazole, bis(2-cyanoethyl) N,N-diisopropylphosphoramidite, elemental sulfur in DCM provides bis-cyanoethyl protected phosphoric acid methyl ester derivative C17 and bis-cyanoethyl protected thiophosphoric acid methyl ester derivative C19, respectively. Deprotection of the bis-cyano ethyl groups is obtained by reaction with a base such as KOH in MeOH followed by acidification using HCl to give phosphoric acid Methyl ester derivative C18 and phosphoric acid methyl ester derivative C20.

The ATX inhibitor chemical compound of the present application may be used to inhibit the action of ATX in vitro or in vivo. In order to inhibit the action of ATX, the inhibitor chemical compound is exposed to ATX in an amount that is sufficient to inhibit the hydrolytic activity of ATX. When used in vivo, the chemical compound is inoculated into an animal that is suffering from a cancer that has a tendency to metastasize. In order to determine the ability of a chemical compound to inhibit the action, of ATX in vitro, the following protocol may be used.

A 10 µM concentration of the compound is added to 2 nM recombinant human ATX and the FRET (Fluorescence Resonance Energy Transfer) ATX substrate FS-3. After 2 hour incubation, the amount of ES-3 that has been hydrolyzed is measured and the residual ATX activity may be expressed as a percent of the vehicle-treated sample less the autolysis of FS-3 in the absence of ATX.

Because cancer metastasis is a complex process that cannot be accurately modeled in vitro, the ability of an ATX inhibitor chemical compound to reduce the incidence or severity of metastasis is difficult to accomplish. Models that utilize cellular monolayers for the invasion of carcinoma cell come the closest to the situation in vivo. Such models are disclosed in the following articles which are incorporated herein by reference: Imamura et al, Jpn. J. Cancer Res., 82 (5):493-496 (1991); Imamura et al, Biochem. Biophys. Res. Commun., 193 (2):497-503 (1993); Mukai et al, Int. J. Cancer, 81 (6): 918-922 (1999); and Mukai et al, FEBS Lett., 484 (2):69-73 (2000). For example, and as disclosed below, the role of ATX in metastasis and the ability of a chemical compound to inhibit ATX in this role may be evaluated using one or both of two different cell monolayers, mouse mesothelium and human vascular endothelium (HUVEC), to examine the role of ATX in the invasion of MM1 hepatocarcinoma cells. The mesothelial monolayer is an accepted model for invasion of body cavities lined by serous cells whereas the HUVEC monolayer is an accepted in vitro model of hematogenous invasion of carcinomas.

In addition, if desired, the reduction of tumor metastasis by an ATX inhibitor chemical compound may be directly determined by utilizing an appropriate animal model, such as disclosed in Baker et al, J. Biol. Chem. 2006, 281 (32):22786-22793 (2006); and Zhang et al, Cancer Res., 69 (13):441-5449 (2009). For example, the syngeneic B16-F10 mouse melanoma model of hematogenous lung metastasis in C57BL/6 mice may be utilized to determine the activity of inhibitors of ATX. According to this protocol, the mice are inoculated with B16-1F10 melanoma cells via the tail vein and are then intraperitoneally injected with a test chemical compound. As a positive control, LPA bromophosphonate (LPA-BP), which has been previously shown to inhibit the metastasis of breast and colon cancers in xenograft models, may be utilized. See, Zhang et al, Cancer Res., 69 (13):441-5449 (2009); and Altman et al Mol. Cancer, 9:140 (2010): On day 21, the mice are sacrificed and the lungs are isolated and any metastatic nodules in the lungs are quantified. As disclosed below, the ATX inhibitor chemical compounds of this application that were tested in this way significantly reduced the number of metastatic foci and their efficacy at this dose was comparable to that of LPA-BP.

As disclosed below, in these cell monolayer systems, the role of ATX in promoting the invasion of cancer cells across mesothelial and vascular endothelial monolayers and the inhibition of such invasion by the ATX inhibitor chemical compounds is shown. Moreover, because the invasion of cancer cells across the monolayers and the inhibition of this invasion by the ATX inhibitor compounds of this application is well correlated with the in vitro test using the FRET substrate, and because in vivo tests on ATX inhibitor compounds showed a reduction in metastasis, this in vitro test and/or the tests using either or both of the cell monolayers are considered to be predictive, for the ability of a chemical compound to inhibit ATX in vivo, such as in a human or veterinary patient. As shown in further detail below, the ATX inhibitor chemical compounds of this application inhibited ATX in vitro in both the test using the FRET substrate and the tests using cell monolayers and in vivo the syngeneic B16-F10 mouse melanoma model of hematogenous lung metastasis.

In addition to their usefulness in the treatment of cancer, the ATX inhibitor chemical compounds of the invention may also be useful as primary or adjunctive therapy in the treatment of other diseases in which at least some part of the symptomatology or effects is influenced by autotaxin. Such diseases include chronic inflammatory diseases, pulmonary fibrosis, rheumatoid arthritis, multiple sclerosis, polyradiculomyelitis, Alzheimer's disease, lupus erythematosus, neuropathic and acute pain, macular degeneration, and conditions associated with angiogenesis mediated by lysophosphatidic acid.

The ATX inhibitor compound may be incorporated into a pharmaceutical formulation for administration to a mammal, such as a human or a veterinary species such as a dog, cat, horse, cow, or sheep, or in non-human primates such as a monkey or ape. The pharmaceutical formulation contains an ATX inhibitor compound or a salt thereof in combination with a pharmaceutically acceptable carrier, excipient or diluent.

The pharmaceutical formulation is administered to the mammalian animal in need thereof in an amount sufficient to inhibit ATX within the body of the animal. The administration of the formulation may be by any means in which autotaxin within the body may be exposed to the ATX inhibitor compound. For example, the formulation may be administered by injection, such as by intravenous, intramuscular, or intraperitoneal injection, or may be administered orally, such as by tablets, capsules, troches, sachets, pills, powders, granules, suspensions, emulsions, solutions, or gels. The pharmaceutical formulations may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The invention is further described in the following non-limiting examples. In the following examples of synthesis of chemical compounds, the numbers of chemical compounds refer to numbered compounds in FIGS. 4 to 9. All starting materials, reagents and solvents were obtained from commercial suppliers and were used without further purification. Reactions were performed under an inert atmosphere of nitrogen, unless otherwise specified. Routine thin-layer chromatography (TLC) was performed on silica gel plates (250 microns) (Analtech, Inc., Newark, Del.). Flash chromatography was conducted on silica gel (grade 60, 230-400 mesh) (Merck & Co., Inc., Whitehouse Station, N.J.). 1H NMR spectra were recorded on a Bruker ARX 300 spectrometer (300 MHz) (Bruker Optics, Inc., Billerica Mass.) or Varian spectrometer (500 MHz) (Agilent Technologies, Santa Clara, Calif.) using DMSO-$d_6$ and $CDCl_3$ as solvents, and spectral data were consistent with assigned structures. Chemical shift values were reported as parts per million ($\delta$), coupling constants (J) are given in Hz, and splitting patterns are designated as follows: s, singlet; d, doublet; t, triplet; q, quartet; m, multiplet. Mass spectra were collected on a Brucker ESQUIRE electrospray/ion (ESI) trap instrument in the positive and negative modes. High-resolution mass (HRMS) measurements were obtained using a Micromass Q-TOF2 mass spectrometer (Waters Corp., Milford, Mass.), Elemental analyses (C, H, N) were performed by Atlantic Microlab, Inc. (Norcross, Ga.), and results were within ±0.4% of the theoretical values for the formula given.

Example 1

Synthesis of Compound 3

1-hexadecanesulfonyl chloride (compound 2) (0.66 g, 2.05 mmol) was added to a mixture of compound 1 (0.5 g, 2.05 mmol) and N,N-diisopropylethylamine (0.04 g, 2.05 mmol) in THF and refluxed for 24 h to obtain compound 3 (Diethyl 4-(hexadecylsulfonamido)benzylphosphonate). The reaction mixture was concentrated under high vacuum and purified by flash column chromatography ($CHCl_3$/MeOH 3:1) to give 0.524 g of pure compound 3 (0.524 g, 48%) as a yellow solid. $^1H$ NMR (300 MHz, [$D_6$] DMSO): $\delta$=9.71 (s, 1H), 7.10-7.25 (overlapping signals, 4H) 3.897-3.948 (p, 4H, J=7.8 Hz), 3.11-3.18 (d, 2H, J=21 Hz) 3.07-2.95 (t, 2H, J=9 Hz) 1.7-1.56 (p, 2H) 1.231 (s, 26H) 1.171-1.123 (t, 6H, J=7.2) 0.9-0.8 (t, 3H); MS (ESI) m/z 530.2 [M−H]$^-$.

Example 2

General Procedure for Synthesis of Phosphonic Acid Analogs Compounds 4, 10, 18, 22, 30a, 30b, 34a, 34b, 37, 41, 42 and 43) (GP 1)

To a suspension of phosphonate derivative (1 equiv) in anhydrous acetonitrile, TMSBr (2.5 equiv) was added and the reaction mixture was refluxed for 1 h. The acetonitrile was then evaporated under reduced pressure and MeOH was added to the residue and stirred for 30 min at RT. The desired product was obtained in good yield after filtration of MeOH solution as a white solid.

Example 3

General Procedure for Synthesis of Compounds 8, 16, 20, 28a, 28b, 32a, 32b and 40 (GP 2)

$PBr_3$ (0.3 equiv) was added slowly under stirring to a solution of alcohol derivative (1 equiv) in anhydrous $CH_2Cl_2$ at 0°

C. The reaction mixture was stirred at RT for 1 h and the formation of the product was monitored by TLC. Water was added at 0° C. to quench the reaction, extracted from $CH_2Cl_2$ and dried over $MgSO_4$. The product was carried on to the next step without further purification.

Example 4

General Procedure for Synthesis of Compounds 9, 17, 21, 29a, 29b, 33a and 33b (GP 3)

Trimethylphosphite (9 equiv) was added to dry bromide derivative (1 equiv) at RT and the mixture was refluxed for 18 h. The trimethylphosphite was evaporated under high vacuum overnight and the crude residue was purified by column chromatography ($CHCl_3$/MeOH 3:1) to give pure compound in quantitative yield.

Example 5

General Procedure for Synthesis of Compounds 13, 25a and 25b (GP 4)

To a mixture of aryl bromide derivative (1 equiv), Palladium(II) acetate (5 mol %), and triethyl amine (1 equiv) in anhydrous DMF was added substituted alkene (1 equiv) successively. The reaction mixture was refluxed for 16 h, filtered on bed of celite and extracted with ethylacetate and water. The compound was purified by flash column chromatography using ethyl acetate and hexane (1:2) mixture.

Example 6

General Procedure for Synthesis of Compound 14, 19, 26a, 26b, 31a and 31b (GP 5)

Anhydrous THF was added to LAH (3 equiv) and stirred for 5 min. To this, a solution of corresponding methyl ester (1 equiv) in THF was added and the mixture was stirred at RT for 4 h. The reaction mixture was cooled to 0° C. and saturated sodium sulfate was added drop-wise to the mixture. The product was then extracted with ethyl acetate and the crude product was purified using flash column Chromatography which, was eluted with ethyl acetate and hexane mixture (1:1).

Example 7

General Procedure for the Synthesis of Compounds 15, 27a and 27b (GP 6)

To a solution of the corresponding alkene of the methyl ester derivative (1 equiv) in MeOH was added catalytic amount of $Pd(OH)_2$/C and the mixture was stirred at RT for 2 h using catalytic amount of hydrogen gas. The completion of reaction was monitored by TLC and the reaction mixture was filtered on a bed of celite. The filtrate was evaporated and purified by column chromatography ($CHCl_3$; MeOH; 30:1)

Example 8

Synthesis of Compound 4

According to general procedure GP 1 in Example 2, compound 4 (4-(Hexadecane-1-sulfonylamino)benzyl phosphonic acid) was obtained as a solid (0.093 gm, 53%). $^1$H NMR (500 MHz, [$D_6$] DMSO): δ=9.66 (d, 1H, J=20 Hz) 7.18-7.08 (m. 4H); 3.04-2.97 (m, 2H); 2.91 (d, 2H, J=20 Hz); 1.64-1.61 (m, 2H) 1.3-1.2 (s, 26H) 0.86-0.83 (t, 3H, J=6 Hz); MS (ESI) m/z 474.0 [M−H]$^-$; Anal Calcd. For $C_{23}H_{42}NO_5PS$: C, 58.08; H, 8.90; N, 2.94. Found: C, 58.31; H, 9.01; N, 2.92.

Example 9

Synthesis of Compound 7

Anhydrous $K_2CO_3$ (0.556 g, 4.02 mmol) and 18-crown-6 (0.02 g, 0.076 mmol) were added to a solution of 5 (0.5 g, 4.03 mmol) in acetone (20 mL) and the mixture was refluxed for 16 h. Acetone was evaporated and the residue was partitioned between water and $CH_2Cl_2$. Pure compound 7 (4-(Tetradecyloxy)phenyl methanol) (1.11 g, 86%) was obtained after flash column chromatography ($CHCl_3$/MeOH 3:1). $^1$H NMR (300 MHz, $CDCl_3$) δ=7.27 (d, 2H); 6.9 (d, 2H); 4.6 (d, 2H); 3.9 (t, 2H); 1.8 (p, 2H); 1.3 (s, 20H); 0.8 (t, 3H); MS (ESI) m/z 319.0 [M−H]$^-$.

Example 10

Synthesis of Compound 9

Compound 9 (Dimethyl-4-(tetradecyloxy)benzylphosphonate) was obtained according to GP 3 in Example 4. $^1$H NMR (300 MHz, $CDCl_3$) δ=7.2 (d, 2H); 6.9 (d, 2H); 3.93 (t, 2H); 3.68 (d, 6H, J=10.8 Hz); 3.1 (d, 2H, J=21 Hz); 1.8 (m, 2H); 1.3 (s, 20H); 0.88 (t, 3H); MS (ESI) m/z 435.4 [M+Na]$^+$.

Example 11

Synthesis of Compound 10

The acid 10 (4-(Tetradecyloxy)benzylphosphonic acid) was prepared similar to the GP 1 in Example 2 and it was obtained as a white solid (0.137 g, 54%). $^1$H NMR (500 MHz, [$D_6$] DMSO): δ=7.135 (d, 2H); 6.82 (d, 2H); 3.91 (t, 2H); 2.8 (d, 2H, J=21 Hz); 1.69 (m, 2H); 1.386 (m, 2H); 1.24 (s, 22H); 0.85 (t, 3H); MS (ESI) m/z 383.0 [M−H]$^-$; Anal calcd. For $C_{21}H_{37}NO_4R$: C, 65.60; H, 9.70. Found C, 65.83; H, 9.81.

Example 12

Synthesis of Compound 13

Compound 13 ((E)-Methyl-4-(pentadec-1-enyl)benzoate) was prepared according to GP 4 in Example 5. $^1$H NMR (300 MHz, $CDCl_3$) δ=7.92-7.5 overlapping protons (m, 4H); 6.4 (m, 1H); 5.4 (m, 1H); 3.92 (s, 3H); 2.1-1.9 (m, 2H); 1.7-1.5 (m, 2H); 1.3 (s, 20H); 0.865 (t, 3H), MS (ESI) m/z 367.3 [M+Na]$^+$.

Example 13

Synthesis of Compound 14

Compound 14 ((E)-4-(Pentadec-1-enyl)phenyl methanol) was synthesized according to GP 5 in Example 6. $^1$H NMR (300 MHz, $CDCl_3$) δ=7.6-7.1 overlapping protons (m, 4H);

6.4-6.2 (m, 1H); 5.5-5.3 (m, 1H); 4.67 (s, 3H); 2.1-1.9 (m, 2H); 1.7-1.5 (m, 2H); 1.27 (s, 20H); 0.895 (t, 3H), MS (ESI) m/z 339.5 [M+Na]$^+$.

Example 14

Synthesis of Compound 15

Compound 15 (Methyl-4-pentadecylbenzoate) was verified with Mass spectrometry and carried on to the next step. MS (ESI) m/z 347.3 ([M+H]); m/z 369.3 [M+Na]$^+$.

Example 15

Synthesis of Compound 17

Compound 17 ((E)-Dimethyl-4-(pentadec-1-enyl)benzylphosphonate) was obtained according to GP 3. $^1$H NMR (300 MHz, CDCl$_3$) δ=7.3-7.1 overlapping protons (m, 4H); 6.4-6.2 (m, 1H); 5.5-5.3 (m, 1H); 3.65 (d, 6H); 3.2 (d, 2H); 2.1-1.9 (m, 2H); 1.7-1.57 (m, 2H); 1.27-1.2 (s, 20H); 0.895 (t, 3H). MS ESI) m/z 431.3 [M+Na]$^+$.

Example 16

Synthesis of Compound 18

Compound 18 ((E)-4-(Pentadec-1-enyl)benzylphosphonic acid) was prepared similar to GP 1 in Example 2 and was obtained as a white powder (0.047 g, 51%). $^1$H NMR (500 MHz, [D$_6$] DMSO): δ=7.281-7.07 overlapping protons (m, 4H); 6.36-6.22 (m, 1H); 5.36 (m, 1H); 2.93 (d, 2H); 2.15 (d, 2H); 1.95 (m, 2H); 1.57 (m, 2H); 1.237 (s, 20H); 0.853 (t, 3H). MS (ESI) m/z 379.0 [M−H]$^−$; HRMS (QTOF) for C$_{22}$H$_{37}$O$_3$P, calcd: 379.2402. found: 379.2412.

Example 17

Synthesis of Compound 19

Compound 19 ((4-Pentadecylphenyl)methanol) was obtained according to GP 5 in Example 6, verified with Mass spectrometry, and carried on to the next step. MS (ESI) m/z 341 [M+Na]$^+$.

Example 18

Synthesis of Compound 21

Compound 21 (Dimethyl-4-pentadecylbenzylphosphonate) was synthesized similar to GP 3 in Example 4. $^1$H NMR (300 MHz, CDCl$_3$) δ=7.4-7.0 overlapping protons (m, 4H); 3.66-3.63 (d, 6H, J=15 Hz); 3.2 (d, 2H); 2.6 (m, 2H); 1.6 (m, 2H); 1.2 (s, 24H); 0.895 (t, 3H). MS (ESI) m/z 433 [M+Na]$^+$.

Example 19

Synthesis of Compound 22 and its Ammonia Salt

Compound 22 (4-Pentadecylbenzylphosphonic acid) was obtained according to GP 1 in Example 2 as a white powder (0.153 g 53%). $^1$H NMR (500 MHz, [D$_6$] DMSO): δ=7.139-7.063 overlapping protons (m, 4H); 2.91 (d, 2H, J=20 Hz); 1.52 (m, 2H); 1.26 (m, 2H); 1.15 (s, 24H); 0.853 (t, 3H). MS (ESI) m/z 381.0 [M−H]$^−$; Anal Calcd. for C$_{22}$H$_{39}$O$_3$P; C, 69.08; H, 10.28. Found C, 69.33; H, 10.52.

4-Pentadecylbenzyl phosphonic acid, ammonia salt was obtained by the following procedure: 2M NH$_3$ in MeOH (0.8 mL) was added to a solution of 4-pentadecylbenzyl phosphonic acid (compound 22, 0.050 g) in MeOH-EtOH (4/1 mL) and the reaction mixture was stirred for 2 h at room temperature and TLC showed the completion of the reaction. The solvents were evaporated under reduced pressure to obtain pure 4-pentadecylbenzyl phosphonic acid ammonia salt as white powder (100% yield). MS(ESI) m/z 381 [M−H]$^−$. Anal calcd. For C$_{22}$H$_{42}$NO$_3$P: C, 66.13; H, 10.60; N, 3.51. Found C, 66.37; H, 10.60; N, 3.58.

Example 20

Synthesis of Compound 25a

According to GP 4 in Example 5 compound 25a ((E)-Methyl-6-(dodec-1-enyl)-2-naphthoate) was prepared. $^1$H NMR (300 MHz, [D$_6$] DMSO): δ=8.582-7.771 overlapping protons (6H); 6.65-6.52 (m, 1H); 5.7-5.2 (m, 1H); 3.91-3.90 (s, 3H); 2.1-1.8 (m, 2H); 1.76-1.55 (m, 2H); 1.209 (s, 14H); 0.856 (t, 3H). MS (ESI) m/z 375.3 [M+Na]$^+$.

Example 21

Synthesis of Compound 25b

Compound 25b ((E)-Methyl-6-(tridec-1-enyl)-2-naphthoate) was prepared similar to GP 4 of Example 5. $^1$H NMR (300 MHz, CDCl$_3$) δ=8.582-7.771 overlapping protons (6H); 6.65-6.52 (m, 1H); 5.7-5.2 (m, 1H); 3.91-3.90 (s, 3H); 2.1-1.8 (m, 2H); 1.76-1.55 (m, 2H); 1.209 (s, 14H); 0.856 (t, 3H). MS (ESI) m/z 389.3 [M+Na]$^+$.

Example 22

Synthesis of Compound 26a

Compound 26a ((E)-6-(Dodec-1-enyl)naphthalen-2-ylmethanol) was obtained according to GP 5 of Example 6. $^1$H NMR (300 MHz, CDCl$_3$) δ=7.9-7.3 overlapping protons (6H); 6.6-6.3 (m, 1H); 5.6-5.4 (m, 1H); 4.814 (s, 2H); 2.35-2.26 (m, 2H); 1.6-1.47 (m, 2H); 1.268 (s, 14H); 0.9 (t, 3H). MS (ESI) m/z 347.3 [M+Na]$^+$.

Example 23

Synthesis of Compound 26b

Compound 26b ((E)-6-Tridec-1-enyl-naphthalen-2-ylmethanol) was prepared according to GP 5 of Example 6. $^1$H NMR (300 MHz, CDCl$_3$) δ=7.72-7.27 overlapping protons (6H); 6.6-6.3 (m, 1); 5.6-5.4 (m, 1H); 4.75 (s, 2H); 2.35-2.26 (m, 2H); 1.6-1.47 (m, 2H); 1.268 (s, 18H); 0.893 (t, 3H). MS (ESI) m/z 361.3 [M+Na]$^+$.

Example 24

Synthesis of Compound 27a

Compound 27a (6-Dodecylnaphthalene-2-carboxylic acid methyl ester) was prepared according to GP 6 of Example 7 and confirmed by Mass spectrometry. MS (ESI) m/z 355 [M+H]$^+$.

Example 25

Synthesis of Compound 27b

Compound 27a (6-Tridecylnaphthalene-2-carboxylic acid methyl ester) was prepared similar to GP 6 of Example 7 and confirmed by Mass spectrometry. MS (ESI) m/z 369.3 [M+H]$^+$.

Example 26

Synthesis of Compound 29a

Compound 29a ((E)-Dimethyl-6-dodec-1-enyl-naphthalen-2-yl-methylphosphonate) was obtained according to GP 3 of Example 4. $^1$H NMR (300 MHz, CDCl$_3$) δ=7.9-7.3 overlapping protons (6H); 6.6-6.3 (m, 1H); 5.6-5.4 (m, 1H); 3.778-3.741 (d, 6H, J=21.6 Hz); 3.34-3.267 (d, 2H, J=21.9 Hz); 2.35-2.26 (m, 2H); 1.6-1.47 (m, 2H); 1.268 (s, 14H); 0.9 (t, 3H). MS (ESI) m/z 439.3 [M+Na]$^+$.

Example 27

Synthesis of Compound 29b

Compound 29b ((E)-Dimethyl-6-tridec-1-enyl-naphthalen-2-yl-methylphosphonate) was obtained similar to GP 3. $^1$H NMR (300 MHz, CDCl$_3$) δ=7.9-7.3 overlapping protons (6H); 6.6-6.3 (m, 1H); 5.6-5.4 (m, 1H); 3.778-3.741 (d, 6H, J=21.6 Hz); 3.34-3.267 (d, 2H, J=21.9 Hz); 2.35-2.26 (m, 2H); 1.6-1.47 (m, 2H); 1.268 (s, 16H); 0.9 (t, 3H). MS (ESI) m/z 453.3 [M+Na]$^+$.

Example 28

Synthesis of Compound 30a

According to GP 1 of Example 2 compound 30a ((E)-6-Dodec-1-enyl-naphthalen-2-yl-methylphosphonic acid) was prepared and was obtained as a white powder (0.027 gm, 52%). $^1$H NMR (500 MHz, [D$_6$] DMSO): δ=7.747-7.329 overlapping protons (6H); 6.556-6.630 (m, 2H); 3.182 (d, 2H, J=21 Hz); 2.221 (m, 2H); 1.468 (m, 2H); 1.255 (s, 14H); 0.836 (t, 3H). MS (ESI) m/z 387.0 [M−H]$^−$; Anal calcd for C$_{23}$H$_{33}$O$_3$P: C, 71.11; H, 8.56. Found: C, 70.73; H, 9.11.

Example 29

Synthesis of Compound 30b

Compound 30b ((E)-6-Tridec-1-enyl-naphthalen-2-yl-methylphosphonic acid) was prepared similar to GP 1 of Example 2 and was obtained as a white powder (0.117 g, 54%). $^1$H NMR (500 MHz, [D$_6$] DMSO): δ=7.811-7.327 overlapping protons (6H); 6.553-6.433 (m, 1H); 5.353 (m, 1H); 3.123-3.080 (d, 2H, J=21.5 Hz); 2.730 (t, 2H); 1.98 (m, 2H); 1.64-1.48 (m, 2H); 1.244 (s, 14H); 0.841 (t, 3H). MS (ESI) m/z 401.0 [M−H]$^−$; HRMS Calcd for C$_{24}$H$_{34}$O$_3$P, 401.2246. found: 401.2249.

Example 30

Synthesis of Compound 31a

Compound 31a (6-Dodecylnaphthalen-2-yl-methanol) was synthesized according to GP 5 of Example 6. $^1$H NMR (300 MHz, CDCl$_3$) a=7.9-7.3 overlapping protons (6H); 4.805 (s, 2H); 2.817-2.792 (m, 2H); 1.833 (m, 2H); 1.372 (s, 16H); 0.963 (t, 3H). MS (ESI) m/z 325.0 [M−H]$^−$; m/z 349.3 [M+Na]$^+$.

Example 31

Synthesis of Compound 31b (31b): Compound 31b (6-Tridecylnaphthalen-2-yl-methanol) was prepared according to GP 5 of Example 6. $^1$H NMR (300 MHz, CDCl$_3$) δ=7.9-7.3 overlapping protons (6H); 4.798 (s, 2H); 2.857-2.7 (m, 2H); 1.833-1.6 (m, 2H); 1.372 (s, 18H); 0.963 (t, 3H). MS (ESI) m/z 363.6 [M+Na]$^+$.

Example 32

Synthesis of Compound 32a

Compound 32a (2-Bromoethyl-6-dodecylnaphthalene) was obtained according to GP 2 of Example 3. $^1$H NMR (300 MHz, CDCl$_3$) δ=7.9-7.3 overlapping protons (6H); 4.696 (s, 2H); 2.817-2.792 (m, 2H); 1.833 (m 2H); 1.372 (s, 18H); 0.968 (t, 3H).

Example 33

Synthesis of Compound 33a

Compound 33a (Dimethyl-6-dodecylnaphthalen-2-yl-methylphosphonate) was prepared to according to GP 3 of Example 4. $^1$H NMR (300 MHz, CDCl$_3$) δ=7.9-7.3 overlapping protons (6H); 3.691-3.655 (d, 6H, J=10.8 Hz); 3.359-3.287 (d, 2H, J=21.6 Hz); 2.817-2.792 (m, 2H); 1.833-1.6 (m, 2H); 1.302 (s, 18H); 0.893 (t, 3H). MS (ESI) m/z 441.3 [M+Na]$^+$.

Example 34

Synthesis of Compound 33b

Compound 33b (Dimethyl-6-tridecylnaphthalen-2-yl-methylphosphonate) was prepared according to GP 3 of Example 4 and confirmed by Mass spectrometry MS(ESI) m/z 455.3 [M+Na]$^+$.

Example 35

Synthesis of Compound 34a

Compound 34a (6-Dodecylnaphthalen-2-yl-methylphosphonic acid) was obtained according to GP 1 of Example 2 and was obtained as a white powder (0.023 g, 49%). $^1$H NMR (500 MHz, [D$_6$] DMSO): δ=7.637-7.326 overlapping protons (6H); 3.13591-3.064 (d, 2H, J=21.3 Hz); 2.927 (m, 2H); 1.641 (m, 2H); 1.263 (s, 18H); 0.849 (t, 3H). MS (ESI) m/z 389.0 [M−H]$^−$. HRMS calcd for C$_{23}$H$_{34}$O$_3$P, 389.2246. found: 389.2237.

Example 36

Synthesis of Compound 34b

Compound 34b (6-Tridecylnaphthalen-2-yl-methylphosphonic acid) was obtained according to GP 1 of Example 2 and was obtained as a white powder (0.036 g, 51%). $^1$H NMR (500 MHz, [D$_6$] DMSO); δ=7.637-7.326 overlapping protons (6H); 3.13591-3.064 (d, 2H, J=21.3 Hz); 2.927 (m, 2H);

1.641 (m, 2H); 1.263 (s, 18H); 0.849 (t, 3H). MS (ESI) m/z 403.0 [M−H]⁻. Anal calcd for $C_{23}H_{33}O_3P$: C, 71.26; H, 9.22. Found: C, 70.82; H, 9.17.

Example 37

Synthesis of Compound 35

Pyridinium dichromate (0.827 g, 2.20 mmol) was added to a solution of 19 (1.00 g, 3.139 mmol) in $CH_2Cl_2$ and stirred the mixture at RT for 16 h. The completion of reaction was checked by TLC. The reaction mixture, was filtered over a bed of silica gel and filtrate was evaporated under reduced, pressure to give compound 35 (4-Pentadecylbenzaldehyde) (0.854 g, 86%), which was used without any further purification for the next step. MS (ESI) m/z 339.3 [M+Na]⁺.

Example 38

Synthesis of Compound 36

Dimethylphosphite (0.547 mL) and triethyl amine (0.357 mL) were added to dry compound 35 (0.953 g, 3.011 mmol) at 0° C. The reaction mixture was stirred at RT for 4 h and the progress of the reaction was monitored by TLC. The crude mixture was purified on a silica gel column using $CHCl_3$: MeOH (30:1) to get compound 36 (Hydroxy-4-pentadecylphenylmethyl phosphonic acid dimethyl ester) in 72% yield (0.926 g). ¹H NMR (500 MHz, $CDCl_3$) δ=7.456-7.149 overlapping protons (4H); 6.040 (d, 1H); 5.03 (d, 1H, J=11.5); 3.77 (d, 6H, J=15); 2.584 (t, 2H), 1.601 (m, 2H); 1.358 (t, 2H); 1.34 (s, 20H); 0.878 (t, 3H). MS (ESI) m/z 449.3 [M+Na]⁺.

Example 39

Synthesis of Compound 37

Compound 37 (Hydroxy-4-pentadecylphenylmethylphosphonic acid) was prepared according to GP 1. of Example 2 and was obtained as a offwhite powder (0.093 g, 52%); ¹H NMR (500 MHz, [$D_6$] DMSO): δ=7.332-7.054 overlapping protons (4H); 6.061 (s, 1H); 4.629 (d, 1H, J=13.5 Hz); 2.584 (overlapping with DMSO, 2H), 1.534 (m, 2H); 1.067 (s, 22H); 0.838 (t, 3H). MS (ESI) m/z 397.0 [M−H]⁻. HRMS calcd for $C_{22}H_{38}O_4P$ [M−H] 397.2508. found 397.2517.

Example 40

Synthesis of Compound 38

To a solution of compound 36 (0.122 g, 0.286 mmol) in ether, diethylaminosulfurtrifluoride (DAST) (0.046 g, 0.286 mmol) was added at 0° C. and stirred the reaction mixture at RT for 1 h. The reaction was quenched by the addition of ice/water, extracted with ether and the crude residue was purified over column chromatography (0.076 gm, 62%) to obtain compound 38 (Fluoro-4-pentadecylphenylmethyl phosphonic acid dimethyl ester). ¹H NMR (500 MHz, $CDCl_3$) δ=7.937 (d, 2H); 7.227 (overlapping protons, 2H); 5.731 (dd, 1H, J=44.5 Hz); 3.747 (d, 6H); 2.610 (t, 2H); 1.602 (m, 2H) 1.228 (s, 24H); 0.878 (t, 3H). MS (ESI) m/z 451.1 [M+Na]⁺.

Example 41

Synthesis of Compound 39

Thionyl chloride (0.047 g, 0.397 mmol) was added to a solution of compound 36 (0.113 g, 0.264 mmol) in anhydrous $CH_2Cl_2$ and refluxed the reaction mixture for 1 h. The solvent was evaporated tinder reduced pressure to afford compound 39 (Chloro-4-pentadecylphenylmethyl phosphonic acid dimethyl ester). MS (ESI) m/z 445.1 ([M⁺]).

Example 42

Synthesis of Compound 40

Compound 40 (Bromo-4-pentadecylphenylmethyl phosphonic acid dimethyl ester) was obtained according to GP 2 of Example 3 and it was used for the next step without further purification.

Example 43

Synthesis of Compound 41

Compound 41 (Fluoro-4-pentadecylphenylmethyl phosphonic acid) was obtained according to GP 1 of Example 2 (0.04 g, 53%). ¹H NMR (500 MHz, [$D_6$] DMSO): δ=7.308 (m, overlapping protons, 4H); 6.669 (s, 1H,); 2.610 (overlapping DMSO peak, 2H); 1.602 (m, 2H) 1.228 (s, 24H); 0.878 (t, 3H). MS (ESI) ink 399.0 [M−H]⁻. HRMS calcd for $C_{22}H_{37}FO_3P$ ([M−H]) 399.2464. found 399.2461.

Example 44

Synthesis of Compound 42

Compound 42 (Chloro-4-pentadecylphenylmethyl phosphonic acid) (0.011 g. 47%) was prepared similar to GP 1 of Example 2. ¹H NMR (500 MHz, $CDCl_3$) δ=7.781 (m, overlapping protons, 4H); 5.050 (s, 1H,); 2.580 (m, 2H); 1.581 (m, 2H) 1.185 (s, 24H); 0.875 (t, 3H). MS (ESI) m/z 415.0 ([M+]). HRMS calcd for $C_{22}H_{37}ClO_3P$ ([M−H]) 415.2169. found: 415.2166.

Example 45

Synthesis of Compound 43

Compound 43 (Bromo-4-pentadecylphenylmethyl phosphonic acid) (0.019 g, 52%) was prepared according to GP 1 of Example 2. ¹H NMR (500 MHz, [$D_6$] DMSO): δ=7.409 (m, overlapping protons, 4H); 4.781 (s, 1H,); 2.580 (overlapping with DMSO, 2H); 1.515 (m, 2H) 1.225 (s, 24H); 0.846 (t, 3H). MS (ESI) m/z 458.9 ([M+]); m/z 460.9 ([M+2]). HRMS calcd for $C_{22}H_{37}BrO_3P$ ([M−H]) 459.1664. found: 459.1664 ([M−H]); 461.1660 ([M+2]).

Example 46

Synthesis of Compound 44

1H-tetrazole (0.149 g, 2.134 mmol) and bis(2-cyanoethyl) N,N-diisopropylphosphoramidite (0.289 g, 1.067 mmol) were added to a solution of compound 19 (0.170 g, 0.534 mmol) in $CH_2Cl_2$ and the mixture was stirred for 1 h followed by addition of hydrogen peroxide (0.12 ml) to give compound 44 (Bis(2-cyanoethyl) 4-pentadecylbenzyl phosphate). MS (ESI) m/z 505.1 ([M+H]).

Example 47

Synthesis of Compound 46

Compound 19 (0.173 g, 0.543 mmol) was treated with a mixture of 1H-tetrazole (0.0760 g, 2.172 mmol) and bis(2- cyanoethyl) N,N-diisopropylphosphoramidite (0.371 g, 1.086 mmol) in anhydrous $CH_2Cl_2$ and stirred for 1 h followed by addition of sulfur (0.034 g, 1.086 mmol) to give compound 46 (O,O-bis(2-cyanoethyl)-O-4-pentadecylbenzyl phosphorothioate). MS (ESI) m/z 543.2 ([M+H]).

Example 48

Synthesis of Compound 45

Compound 44 (1 equiv) was dissolved in methanol and 1N methanolic KOH (1 equiv) was added to the reaction mixture. The completion of the reaction was monitored by TLC. The methanol was evaporated and 1N HCl was added and the compound was extracted with $CHCl_3$. Purification of the crude residue by column chromatography (30:1 $CHCl_3$: MeOH) gave desired compound 45 (4-pentadecylbenzyl dihydrogen phosphate).

Compound 45 was obtained as a solid (0.087 g, 77%). $^1$HNMR (500 MHz, CD3OD) δ=7.337-7.123 (m, overlapping protons, 4H); 5.075 (overlapping with $CD_3OD$ peak, 2H,); 2.598 (t, 2H) 1.593 (m, 2H) 1.184 (s, 24H); 0.890 (t, 3H) MS (ESI) m/z 397.0 [M–H]$^-$. HRMS calcd for $C_{22}H_{38}O_4P$ ([M–H]) 397.2508. Found: 397.2511.

Example 49

Synthesis of Compound 47

Compound 46 (1 equiv) was dissolved in methanol and 1N methanolic KOH (1 equiv) was added to the reaction mixture. The completion of the reaction was monitored by TLC. The methanol was evaporated and 1N HCl was added and the compound was extracted with $CHCl_3$. Purification of the crude residue by column chromatography (30:1 $CHCl_3$: MeOH) gave desired compound 47 (O-4-pentadecylbenzyl O,O-dihydrogen phosphorothioate).

Compound 47 was obtained as a solid (0.073 g, 83%). $^1$HNMR (500 MHz, $CD_3OD$) δ=7.321-7.129 (m, overlapping protons, 4H); 4.955 (d, 2H, J=4 Hz); 3.581 (t, 2H); 2.586 (t, 2H); 1.580 (m, 2H); 1.199 (s, 24H); 0.889 (t, 3H) MS (ESI) m/z 413.0 [M–H]$^-$. HRMS calcd for $C_{22}H_{38}O_3PS$ ([M–H]) 413.2279. Found: 413.2281.

In the following examples showing the testing of the chemical compounds of this application, lysophosphatidic acid (LPA) (18:1), lysophosphatidylcholine (LPC) (18:1), and Sphingosine-1-phosphate (S1P) were purchased from Avanti Polar Lipids (Alabaster, Ala.). For calcium mobilization assays, LPA, S1P, and the test compounds were prepared as 1 mM stock solutions in phosphate-buffered saline (PBS) in an equimolar complex with charcoal-stripped, fatty acid free bovine serum albumin (BSA; Sigma, St. Louis, Mo.). The fluorescent ATX substrate FS-3 was purchased from Echelon Biosciences (Salt Lake City, Utah).

The results of the testing described below in Examples 50 to 52 are shown for benzylphosphonic acid chemical compounds of this application in Table 1 and for naphthylphosphonic acid chemical compounds of this application in Table 2.

TABLE 1

| | | | | ATX | | | | | NPP6 | NPP7 |
|---|---|---|---|---|---|---|---|---|---|---|
| Compound | X | Y | R | Activity; % control (10 μM) | IC$_{50}$ (μM) | Mechanism of inhibition | K$_i$ (μM) | K$_i$' (μM) | Activity, % control (10 μM) | Activity, % control (10 μM) |
| S32826 | O | CH$_2$ | HN-C(=O)-C$_{13}$H$_{27}$ | 2.6 | ND | ND | N/A | N/A | 102.1 | 101.2 |
| 4 | O | CH$_2$ | HN-S(=O)$_2$-C$_{16}$H$_{33}$ | 24.1 | ND | ND | N/A | N/A | 102.0 | 93.5 |
| 10 | O | CH$_2$ | O-C$_{13}$H$_{27}$ | 30.4 | ND | ND | N/A | N/A | 102.0 | 100.6 |
| 18 | O | CH$_2$ | CH=CH-C$_{13}$H$_{27}$ | 18.8 | ND | ND | N/A | N/A | 104.0 | 97.7 |
| 22 | O | CH$_2$ | C$_{13}$H$_{27}$ | 5.2 | 0.17 | Mixed | 0.27 | 0.28 | 96.5 | 96.7 |
| 37 | O | CHOH | C$_{13}$H$_{27}$ | 9.2 | 0.73 | Mixed | 0.45 | 0.70 | 99.6 | 101.0 |
| 41 | O | CHF | C$_{13}$H$_{27}$ | 42.3 | 17.9 | Mixed | 4.97 | 5.54 | 101.1 | 102.6 |
| 42 | O | CHCl | C$_{13}$H$_{27}$ | 117.9 | ND | ND | N/A | N/A | 100.6 | 99.9 |

TABLE 1-continued

[Structure: HO-P(=X)(OH)-Y-C6H4-R]

| Compound | X | Y | R | ATX Activity; % control (10 μM) | ATX IC$_{50}$ (μM) | ATX Mechanism of inhibition | ATX K$_i$ (μM) | ATX K$_i'$ (μM) | NPP6 Activity, % control (10 μM) | NPP7 Activity, % control (10 μM) |
|---|---|---|---|---|---|---|---|---|---|---|
| 43 | O | CHBr | C$_{13}$H$_{27}$ | 60.1 | 10.1 | Mixed | 6.10 | 2.97 | 99.3 | 99.5 |
| 45 | O | O—CH$_2$ | C$_{13}$H$_{27}$ | 85.2 | ND | ND | N/A | N/A | 100.9 | 98.8 |
| 47 | S | O—CH$_2$ | C$_{13}$H$_{27}$ | 15.2 | 1.54 | Mixed | 4.45 | 4.43 | 98.8 | 92.9 |

ND = not determined,
NA = not applicable because the mechanism of inhibition was not determined for this compound

TABLE 2

[Structure: HO-P(=X)(OH)-Y-naphthyl-R$_1$]

| Compound | X | Y | R$_1$ | ATX Activity, % control (10 μM) | ATX IC$_{50}$ (μM) | ATX Mechanism of inhibition | ATX K$_i$ (μM) | ATX K$_i'$ (μM) | NPP6 Activity, % control (10 μM) | NPP7 Activity, % control (10 μM) |
|---|---|---|---|---|---|---|---|---|---|---|
| 30a | O | CH$_2$ | C$_{10}$H$_{21}$ | 61.3 | ND | ND | N/A | N/A | 103.1 | 100.0 |
| 30b | O | CH$_2$ | C$_{11}$H$_{23}$ | 17.3 | 1.40 | MIXED | 1.50 | 1.01 | 104.1 | 96.5 |
| 34a | O | CH$_2$ | C$_{10}$H$_{21}$ | 19.9 | ND | ND | N/A | N/A | 101.0 | 98.8 |
| 34b | O | CH$_2$ | C$_{11}$H$_{23}$ | 50.8 | ND | ND | N/A | N/A | 100.0 | 94.7 |

ND = not determined,
NA = not applicable because the mechanism of inhibition was not determined for this compound Example 50

Autotaxin Inhibition Screening Assay

As the first level of screen, 50 μl of recombinant-ATX (2 nM in final concentration) in assay buffer [(Tris 50 mM, NaCl 140 mM, KCl 5 mM, CaCl$_2$ 1 mM, MgCl$_2$ 1 mM (pH 8.0)] was mixed with 25 μL of FS-3 (Echelon Biosciences, Inc., Salt lake city, Utah), final concentration 1 μM, and 25 μl of test compound was dissolved in assay buffer with 40 μM bovine serum albumin (Sigma, St. Louis, Mo.) in 96-well Costar black-well plate. FS-3 fluorescence at excitation and emission wavelengths of 485 and 538 nm, respectively, were monitored using a FLEXstation II (Molecular Devices, Sunnyvale, Calif.) for 2 h of incubation at 37° C. The differences between time 0 and 120 min were calculated individually and normalized to the vehicle control. The mean±SD of triplicate samples was expressed as percentage of ATX activity. The ATX activity in the presence of the test compounds was compared to vehicle using the Student's and p<0.05 was considered significant.

The first level of testing was done using 10 μM concentrations of the compounds shown in Tables 1 and 2 added to 2 nM recombinant human ATX and the FRET substrate FS-3. After a 2 h incubation the amount of FS3 hydrolyzed was measured and the residual ATX activity was expressed as a percent of the vehicle-treated sample less the autolysis of FS3 in the absence of ATX. In this assay, S32826 reduced the amount of FS3 hydrolyzed by 97% (Table 1a & b). Among the 4-substituted benzyl phosphonic acid analogs, compound 22 showed 95% inhibition of FS3 hydrolysis (Table 1) and compound 30b from the 6-substituted naphthalene-2yl-methyl phosphonic acid series reduced FS3 hydrolysis by 83% (Table 2). Dose-response curves were generated with compounds S32836, 22 and 30b and compared to the feedback inhibition of the ATX product LPA (FIG. 10). Each of these three compounds dose-dependently and completely inhibited ATX.

Example 51

Mechanism of Autotaxin Inhibition

The mechanism of inhibition of ATX was determined using recombinant, purified human ATX and FS-3. Final ATX and FS-3 concentrations were 8.3 nM and 1 µM, respectively and the assay buffer with 15 µM fatty acid tree BSA. To calculate $IC_{50}$, full dose responses were determined for the test compounds. In addition, the mechanism of inhibition of ATX-mediate hydrolysis of FS-3 was determined by varying the concentration (0.3 µM to 20 µM) of substrate in the presence of three concentrations of each inhibitor (0, 0.5× and 2× ($IC_{50}$)). Kinetic data including $V_{max}$ and $K_m$ were determined using KaleidaGraph 4.0 (version 4.03, Synergy Software, Reading, Pa.) after the plots of initial velocities versus substrate concentration in the absence or presence of inhibitors were fit to the following equation $y=m_1*m_2*x/(1+m_2*x)$, where $K_m=1/m_2$ and $V_{max}=m_1$. The average $K_m$ for ATX-mediated FS-3 hydrolysis was determined, to be 2.3 µM and was used in the following calculations. Simultaneous non-linear regression, using, WinNonLin® 6.1 (Pharsight, Mountain View, Calif.) was used to assign the mechanism of inhibition. $K_i$ and $K_i'$ values (the affinity for free enzyme and enzyme substrate complex, respectively) were determined by calculating the lowest averaged percent residuals for each mechanism derived from curve fitting using the Michealis-Menten equations for competitive, uncompetitive, mixed-mode, and non-competitive inhibition. These experiments showed that these compounds uniformly displayed similar $K_i$ and $K_i'$ values which is consistent with a mixed-mode type mechanism of inhibition.

Example 52

NPP-6 and NPP-7 Inhibition Assay

NPP6 and NPP7 are the only NPP isoforms other than ATX that are known to utilize lysophospholipid phosphodiesters as substrates. Therefore, the specificity of the chemical compounds of the invention regarding ATX was addressed by determining the activity of NPP6 and NPP7 in the presence and absence of these analogs.

Inhibition of NPP6 and NPP7 was evaluated using recombinant, purified proteins, the synthetic substrate para-nitro-phenylphosphocholine (pNPPC) and a Synergy II plate reader (BioTek, Winooski, Vt.). The final concentration of each enzyme was 8.3 nM and pNPPC was 10 µM. All analogs were tested at single 10 µM concentrations. Absorbance of liberated para-nitrophenol at 405 nm was determined up to 1 hour (where responses were linear) and was normalized to vehicle control.

As shown in Tables 1 and 2, none of the analogs tested blocked the activity of NPP6 or NPP7 by greater than 10% at a single 10 µM dose.

Example 53

Profile of LPA Receptors and ATX Transcripts in Cancer Cells

Cancer metastasis is a complex process that cannon be accurately modeled in vitro. Models that utilize cellular monolayers for the invasion of carcinoma cell come the closest to the situation in vivo. Two different cell monolayers, mouse mesothelium and human vascular endothelium were used to examine the role of ATX in the invasion of MM1 hepatocarcinoma cells and the reduction of such invasion by the chemical compounds of the present application. The mesothelial monolayer is an accepted model for invasion of body cavities lined by serous cells whereas, the HUVEC monolayer is considered to be an in vitro model of hematogenous invasion of carcinomas.

Highly invasive MM1 cells originally isolated from the AH130 rat hepatoma cells were utilized in these studies. The cells were grown in suspension in DMEM supplemented with 10% fetal bovine serum, 2 mM glutamine, 100 units/ml penicillin and 10 µg/ml streptoinycin. Mesothelial cells were isolated and cultured from C57BL/6 mice. Human umbilical cord vascular endothelial cells (HUVEC) were obtained from VEC Technologies Inc., (Rensselaer, N.Y., USA) and were grown in MCDB-131 complete medium containing 10% fetal bovine serum. 90 µg/ml heparin, 10 ng/ml EGF, 1 µg/ml hydrocortisone, 0.2 mg/ml EndoGrowth supplement, 100 units/ml penicillin G, 100 µg/ml streptomycin and 25 µg/ml amphotericin B (all from VEC Technologies). Tumor cell invasion was performed by seeding $1.3 \times 10^5$ HUVECs (passage 7) into each well of a 12-well plate pre-coated with 0.2% gelatin (Sigma) and cultured for 2 days to form a confluent monolayer. Mesothelial cells harvested from two-three mice were initially plated in 6-well plates and grown to confluency in DMEM medium supplemented with 10% fetal bovine serum in the presence of 100 units/ml penicillin G and 10 µg/ml streptomycin. When confluent, the mesothelial cells were split into three equal aliquots (~$5 \times 10^4$ cells each) and plated to three wells of a 12-well plate and grown to confluence.

The mesothelial and HUVEC cells of the monolayer and the invading MM1 cells express different levels of ATX, as shown in FIG. 11, panels A to C. Quantitative real-time PCR performed with mRNA isolated from MM1, mesothelium and HUVEC cells showed that the primary source of ATX is the MM1 cell as the other two cell types showed very low expression. MM1 cells showed robust expression of transcripts encoding the P2Y family, of LPA receptors and $LPA_2$ in the EDG receptor subfamily. In mesothelial cells $LPA_2$ is the predominant receptor whereas, in HUVECs it is the $LPA_5$ receptor.

Example 54

Reduction of Invasion of Tissue Monolayers

Invasion of MM1 cells of Example 53 was determined and the effect of compounds of the present application in reducing the invasion was determined. For all invasion assays, MM1 cells were pre-stained with 2 µg/ml calcein AM (Invitrogen, USA) for 2 h, rinsed once, and seeded at a density of $5 \times 10^4$ cells/well over the monolayers. Tumor cells were left to invade the HUVEC monolayer for 24 h in MCDB-131 complete media containing 1% serum with or without addition of 1.5 µM LPC. MM1 cells were plated on the mesothelial monolayers in 2% fetal bovine serum-supplemented DMEM medium in the presence of 100 units/ml penicillin G and 10 µg/ml streptomycin with or without 1.5 µM LPC (5 µM for the mesothelium cells) and invasion was allowed to proceed for 20 h. The day after MM1 cell seeding, non-invaded tumor cells were removed by repeated five rinses of the HUVEC monolayer (three rinses for the mesothelial monolayers) with PBS (containing $Ca^{2+}$ and $Mg^{2+}$) followed by fixation with 10% buffered formalin. The number of tumor cells that penetrated the monolayer was photographed under a NIKON TiU inverted microscope using phase-contrast and fluorescence illumination in a minimum of five non-overlapping fields at 100× magnification. The fluorescent images were overlayed on top of the phase contrast images using the Elements BR software (version 3.1x) and the invaded MM1 cells showing the characteristic flattened morphology in the plane of focus underneath the monolayer were counted. For the invasion assay, LPC dissolved in chloroform was dried, redissolved in 1 mM charcoal-stripped BSA in PBS and added immediately to the HUVEC or mesothelium monolayer and co-cultured with MM1 cells with or without the ATX inhibitors. The final BSA concentration was 30 µM.

The results are shown graphically in FIG. 12, panels D and E, and FIG. 14. Addition of LPC to the co-culture increases invasion in a dose-dependent manner, as shown in FIG. 12d. Because it is conceived that inhibition of ATX by the compounds of the present application will attenuate LPA production in situ and reduce invasion of MM1 carcinoma cells through the mesothelial and HUVEC monolayers, compounds 22 and 30b were applied with or without LPC to the co-cultures and the number of invading cells was quantified after 24 h of the co-culture. The results are shown for the mesothelial cell monolayer in FIG. 12e and for HUVEC monolayer in FIG. 14. Both compounds inhibited MM1 cell invasion of the mesothelial monolayer, reaching a complete inhibition of LPA and likely ATX-dependent invasion above 3 µM. Similarly to that seen for the invasion of murine mesothelial monolayers, compounds 22 and 30b dose-dependently inhibited the LPC-dependent invasion of the HUVEC monolayer whereas, the compounds alone did not reduce the basal rate of invasion. These results provide evidence that the inhibition of ATX in situ can fully inhibit LPC-dependent invasion of carcinoma cells.

Example 55

Reduction of Metastasis In Vivo

Eight-week-old female C57Bl/6 mice were injected via the tail vein with $5 \times 10^4$ B16-1F10 melanoma cells/animal via and divided randomly into 4 groups. Each group then received via peritoneal injection a selective ATX inhibitor, either compound 22 or, compound 30b, or with dual ATX and LPA receptor antagonist LPA-BP that we showed previously to inhibit the metastasis of breast and colon cancers in xenograft models. Zhang et al, *Cancer Res.*, 69 (13):5441-5449 (2009). All injections were dosed at 0.5 mg/kg/injection 30 min after the B16-F10 injection and daily for an additional 10 days. Control mice were dosed with vehicle (PBS with 1% DMSO). Animals in all groups were monitored for another 10 days without treatment. At day 21, all mice were sacrificed and lungs were harvested, inflated, and fixed with 10% formalin. The number of metastatic nodules on the lung surface was counted. The number of lung nodules was compared to vehicle treated group by one-way ANOVA followed by Newman-Keuls multiple comparison test and $p<0.05$ was considered significant.

As shown in FIG. 13, compounds of the present application significantly reduced the number of metastatic foci, and their efficacy at this dose was comparable to that of LPA-BP, a known inhibitor of metastasis.

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A chemical compound selected from the group consisting of (1) 4-(Hexadecane-1-sulfonylamino)benzyl phosphonic acid; (2) (E)-4-(Pentadec-1-enyl)benzylphosphonic acid; (3) 4-Pentadecylbenzylphosphonic acid; (4) Hydroxy-4-pentadecylphenylmethylphosphonic acid; (5) Fluoro-4-pentadecylphenylmethyl phosphonic acid; (6) Chloro-4-pentadecylphenylmethyl phosphonic acid; (7) Bromo-4-pentadecylphenylmethyl phosphonic acid; (8) 4-pentadecylbenzyl dihydrogen phosphate; and (9) O-4-pentadecylbenzyl O,O-dihydrogen phosphorothioate.

2. The chemical compound of claim 1 which is 4-Pentadecylbenzyl phosphonic acid, ammonia salt.

3. A pharmaceutical composition comprising the chemical compound of claim 1 or a salt thereof admixed with a pharmaceutically acceptable carrier, excipient or diluent.

* * * * *